US007888379B2

(12) United States Patent
Quattropani et al.

(10) Patent No.: US 7,888,379 B2
(45) Date of Patent: Feb. 15, 2011

(54) THIAZOLE DERIVATIVES AND USE THEREOF

(75) Inventors: Anna Quattropani, Geneva (CH); David Covini, Neydens (FR); Vincent Pomel, Groisy (FR); Jerome Dorbais, Annecy (FR); Thomas Rueckle, Geneva (CH)

(73) Assignee: Merck Serono SA, Coinsins, Vaud (CH)

( * ) Notice: Subject to any disclaimer, the term of this patent is extended or adjusted under 35 U.S.C. 154(b) by 400 days.

(21) Appl. No.: 11/915,508

(22) PCT Filed: May 24, 2006

(86) PCT No.: PCT/EP2006/062602

§ 371 (c)(1),
(2), (4) Date: Nov. 26, 2007

(87) PCT Pub. No.: WO2006/125807

PCT Pub. Date: Nov. 30, 2006

(65) Prior Publication Data

US 2008/0200463 A1 Aug. 21, 2008

Related U.S. Application Data

(60) Provisional application No. 60/686,266, filed on Jun. 1, 2005.

(30) Foreign Application Priority Data

May 24, 2005 (EP) .................................. 05104418

(51) Int. Cl.
*A61K 31/426* (2006.01)
*A61K 31/5377* (2006.01)
*C07D 277/20* (2006.01)
*C07D 413/14* (2006.01)

(52) U.S. Cl. .................. 514/370; 548/146; 548/190; 548/194; 544/106; 544/111; 544/132; 514/365; 514/231.5; 514/235.5; 546/184; 546/192; 546/209

(58) Field of Classification Search .............. 544/106, 544/111, 133, 132; 548/146, 190, 193, 194; 514/231.5, 235.5, 236.8, 365, 370, 371; 546/184, 546/192, 209

See application file for complete search history.

(56) References Cited

U.S. PATENT DOCUMENTS

| | | | | |
|---|---|---|---|---|
| 6,586,423 B2 * | 7/2003 | Bilodeau et al. | ....... | 514/217.04 |
| 6,586,424 B2 * | 7/2003 | Bilodeau et al. | ....... | 514/217.04 |
| 7,163,952 B2 | 1/2007 | Inaba et al. | | |
| 2003/0158199 A1 | 8/2003 | Stieber et al. | | |
| 2008/0188531 A1 | 8/2008 | Quattropani et al. | | |
| 2008/0221180 A1 | 9/2008 | Quattropani et al. | | |
| 2009/0029997 A1 | 1/2009 | Quattropani et al. | | |

FOREIGN PATENT DOCUMENTS

| | | |
|---|---|---|
| EP | 0 117 082 | 8/1984 |
| WO | WO 00/75120 | 12/2000 |
| WO | WO 01/17995 | 3/2001 |
| WO | WO 03/072557 | 9/2003 |
| WO | WO 2004/033439 | 4/2004 |
| WO | WO 2004/052286 | 6/2004 |
| WO | WO 2004/078754 | 9/2004 |
| WO | WO 2004/096797 | 11/2004 |
| WO | WO 2005/021519 A2 | 3/2005 |
| WO | WO 2005/047273 | 5/2005 |
| WO | WO 2005/068444 | 7/2005 |
| WO | WO 2006/051270 | 5/2006 |

OTHER PUBLICATIONS

Bilodeau et al (2001): STN International HCAPLUS database, (Columbus, Ohio), Accession No. 2001:185751.*
Bold et al (2005): STN International HCAPLUS database, (Columbus, Ohio), Accession No. 2005:451371.*
Beaton, C. M. et al. "Some Derivatives of 2- and 3-Phenylthiophen" *J. Chem. Soc.*, 1976, pp. 2355-2563, vol. I.
Bellina, F. et al. "Palladium Catalysts for the Suzuki Cross-Coupling Reaction: An Overview of Recent Advances" *Synthesis*, 2004, pp. 2419-2440, No. 15.
Brummond, K. M. et al. "Solid-Phase Synthesis of BRL 49653" *J. Org. Chem.*, 1999, pp. 1723-1726, vol. 64.
Cantley, L.C. "The Phosphoinositide 3-Kinase Pathway" *Science*, May 31, 2002, pp. 1655-1657, vol. 296.
Fraser, J. D. et al. "Regulation of Interleukin-2 Gene Enhancer Activity by the T Cell Accessory Molecule CD28" *Science*, Jan. 18, 1991, pp. 313-316, vol. 251.
Fruman, D.A. et al. "Phosphoinositide Kinases" *Annu. Rev. Biochem.*, 1998, pp. 481-507, vol. 67.
Gerard, C. et al. "Chemokines and disease" *Nature Immunology*, Feb. 2001, pp. 108-115, vol. 2, No. 2.
Grant, S. "Targeted Therapies in Cancer—Second International Congress" *Current Drugs*, 2003, pp. 946-948, vol. 6, No. 10.
Hirsch, E. et al. "Central Role for G Protein-Coupled Phosphoinositide 3-Kinase γ in Inflammation" *Science*, Feb. 11, 2000, pp. 1049-1053, vol. 287.
Hirsch, E. et al. "Resistance to thromboembolism in PI3 Kγ-deficient mice" *FASEB J.*, 2001, pp. 2019-2021, vol. 15, No. 11.
Kodomari, M. et al. "One-pot synthesis of 2-aminothiazoles using supported reagents" *Tetrahedron Letters*, 2002, pp. 1717-1720, vol. 43.
Laffargue, M. et al. "Phosphoninositide 3-Kinase γ Is an Essential Amplifier of Mast Cell Function" *Immunity*, Mar. 2002, pp. 441-451, vol. 16.
Lawlor, M. A. et al. "PKB/Akt: a key mediator of cell proliferation, survival and insulin responses?" *Journal of Cell Science*, 2001, pp. 2903-2910, vol. 114.

(Continued)

*Primary Examiner*—Golam M Shameem
(74) *Attorney, Agent, or Firm*—Saliwanchik, Lloyd & Eisenschenk

(57) ABSTRACT

The present invention is related to thiazole derivatives of Formula (I) in particular for the treatment and/or prophylaxis of autoimmune disorders and/or inflammatory diseases, cardiovascular diseases, neurodegenerative diseases, bacterial or viral infections, kidney diseases, platelet aggregation, cancer, transplantation, graft rejection or lung injuries.

11 Claims, No Drawings

OTHER PUBLICATIONS

Parker, P. J. "PI 3-kinase puts GTP on the Rac" *Current Biology*, 1995, pp. 577-599, vol. 5, No. 6.

Stein, R. C. et al. "PI3-kinase inhibition: a target for drug development?" *Molecular Medicine Today*, Sep. 2000, pp. 347-357, vol. 6.

Thelen, M. et al. "Wortmannin binds specifically to 1-phosphatidylinositol 3-kinase while inhibiting guanine nucleotide-binding protein-coupled receptor signaling in neutrophil leukocytes" *Proc. Natl. Acad. Sci. USA*, May 1994, pp. 4960-4964, vol. 91.

Toker, a. "Phosphoinositides and signal transduction" *Cellular and Molecular Life Sciences*, 2002, pp. 761-779, vol. 59.

Vanhaesebroeck, B. et al. "Phosphoinositide 3-kinases: a conserved family of signal transducers" *Trends Biochem. Science*, Jul. 1997, pp. 267-272, vol. 22.

Vanhaesebroeck, B. et al. "Synthesis and Function of 3-Phosphorylated Inositol Lipids" *Ann. Rev. Biochem.*, 2001, pp. 535-602, vol. 70.

Wymann, M. P. et al. "Lipids on the move: phosphoinositide 3-kinases in leukocyte function" *Immunology Today*, Jun. 2000, pp. 260-264, vol. 21, No. 6.

Yao, R. et al. "Requirement for Phosphatidylinositol-3 Kinase in the Prevention of Apoptosis by Nerve Growth Factor" *Science*, Mar. 31, 1995, pp. 2003-2005, vol. 267.

Guarna, A. et al. "Synthesis and Reactivity of Bicycles Derived from Tartaric Acid and α-Amino Acids: A Novel Class of Conformationally Constrained Dipeptide Isosteres Based upon Enantiopure 3-Aza-6, 8-dioxabicyclo [3.2.1] octane-7-carboxylic Acid" *J. Org. Chem.*, 1999, pp. 7347-7364, vol. 64.

Herr, R. J. et al. "A Convenient Method for the Preparation of Primary and Symmetrical N,N'- Disubstituted Thioureas" *Synthesis*, 2000, pp. 1569-1574, No. 11.

Pirrung, M.C. et al. "Trityl Isothiocyanate Support for Solid-Phase Synthesis" *J. Comb. Chem.*, 2001, pp. 90-96, vol. 3.

Sawhney, S. N. et al. "Thiazole Derivatives: Part I—Synthesis & Anti-Inflammatory Activity of some 2'-Alkyl/Aryl-2-Aryl-4-Methyl-4'5-Bithiazolyls & 2'Amino-Substituted Amino-2-Aryl-4-Methyl-4'5-Bithiazolyls" *Indian Journal of Chemistry*, Jul. 1976, pp. 552-555, vol. 14B, No. 7.

Sayed, S.M. et al. "Synthesis and Reactivity of Cyanomethyl 2-Amino-4-methylthiazolyl Ketone. A Facile Synthesis of Novel Pyrazolo [5,1-c] 1,2,4-triazine, 1,2,4-Triazolo [5,1-c] 1, 2,4,-triazine, 1,2,4-Triazino [4,3-a] benzimidazole, Pyridazine-6-imine and 6-Oxopyridazinone Derivatives" *Heteroatom Chemistry*, 1999, pp. 385-390, vol. 10, No. 5.

Wilson, K.J. et al. "Synthesis of Thiophene-2-carboxamidines Containing 2-Amino-thiazoles and their Biological Evaluation as Urokinase Inhibitors" *Bioorganic & Medicinal Chemistry Letters*, 2001, pp. 915-918, vol. 11.

Wittenberger, S.J. et al. "Dialkyltin Oxide Mediated Addition of Trimethylsilyl Azide to Nitriles. A Novel Preparation of 5-Substituted Tetrazoles" *J.Org. Chem.*, 1993, pp. 4139-4141, vol. 58.

Inaba, T. et al., 2002, CAS: 136:177998, pp. 1-4.

Office Action dated Apr. 6, 2010 in U.S. Appl. No. 11/915,521, filed Nov. 26, 2007.

Office Action dated Nov. 24, 2009 in U.S. Appl. No. 11/915,476, filed Nov. 26, 2007.

Allowed claims in U.S. Appl. No. 11/915,476, filed Nov. 26, 2007.

Pending claims in U.S. Appl. No. 11/915,521, filed Nov. 26, 2007.

Pending claims in U.S. Appl. No. 12/159,663, filed Jun. 30, 2008.

* cited by examiner

THIAZOLE DERIVATIVES AND USE THEREOF

CROSS-REFERENCE TO RELATED APPLICATION

This application is the U.S. national stage application of International Patent Application No. PCT/EP2006/062602, filed May 24, 2006, which claims the benefit of U.S. Provisional Patent Application No. 60/686,266, filed Jun. 1, 2005, the disclosures of which are hereby incorporated by reference in their entireties, including all figures, tables and amino acid or nucleic acid sequences.

FIELD OF THE INVENTION

This present invention is related to the use of thiazole derivatives of Formula (I) for the treatment and/or prophylaxis of autoimmune disorders and/or inflammatory diseases, cardiovascular diseases, neurodegenerative diseases, bacterial or viral infections, allergy, asthma, pancreatitis, multi-organ failure, kidney diseases, platelet aggregation, cancer, transplantation, sperm motility, erythrocyte deficiency, sperm motility, graft rejection or lung injuries. Specifically, the present invention is related to thiazole derivatives for the modulation, notably the inhibition of the activity or function of the phosphoinositide-3-kinases, PI3Ks.

BACKGROUND OF THE INVENTION

Phosphoinositide 3-kinases (PI3Ks) have a critical signaling role in cell proliferation, cell survival, vascularization, membrane trafficking, glucose transport, neurite outgrowth, membrane ruffling, superoxide production, actin reorganization and chemotaxis (Cantley, 2000, *Science*, 296, 1655-1657 and Vanhaesebroeck et al., 2001, *Annu. Rev. Biochem.*, 70, 535-602).

The term PI3K is given to a family of lipid kinases which, in mammals, consists of eight identified PI3Ks that are divided into three sub-families according to their structure and their substrate specificity.

Class I group of PI3Ks consists of two sub-groups, Class IA and Class IB.

Class IA consists of an 85 kDa regulatory unit (responsible for protein-protein interactions via the interaction of Src homology 2 (SH2) domain with phosphotyrosine residues of other proteins) and a catalytic sub-unit of 110 kDa. Three catalytic forms (p110α, p110β and p110δ) and five regulatory isoforms (p85α, p85β, p55γ, p55α and p50α) exist for this class.

Class IB are stimulated by G protein βγ sub-units of heterodimeric G proteins. The only characterized member of Class IB is PI3Kγ (p110γ catalytic sub-unit complexed with a 101-kDa regulatory protein, p101).

Class II PI3Ks comprises α, β and γ isoforms, which are approximately of 170 kDa and characterized by the presence of a C-terminal C2 domain.

Class III PI3Ks includes the phosphatidylinositol specific 3-kinases.

The evolutionary conserved isoforms p110α and β are ubiquitously expressed, while δ and γ are more specifically expressed in the haematopoetic cell system, smooth muscle cells, myocytes and endothelial cells (Vanhaesebroeck et al., 1997, *Trends Biochem Sci.*, 22(7), 267-72). Their expression might also be regulated in an inducible manner depending on the cellular-, tissue type and stimuli as well as disease context.

PI3Ks are enzymes involved in phospholipid signaling and are activated in response to a variety of extra-cellular signals such as growth factors, mitogens, integrins (cell-cell interactions) hormones, cytokines, viruses and neurotransmitters and also by intra-cellular cross regulation by other signaling molecules (cross-talk, where the original signal can activate some parallel pathways that in a second step transmit signals to PI3Ks by intra-cellular signaling events), such as small GTPases, kinases or phosphatases for example.

Phosphatidylinositol (PtdIns) is the basic building block for the intracellular inositol lipids in eukaryotic cells, consisting of D-myo-inositol-1-phosphate (Ins1P) linked via its phosphate group to diacylglycerol. The inositol head group of PtdIns has five free hydroxy groups and three of these are found to be phosphorylated in cells in different combinations. PtdIns and its phosphorylated derivatives are collectively referred as inositol phospholipids or phosphoinositides (PIs). Eight PI species have been documented in eukaryotic cells (Vanhaesebroeck et al., 2001, above). PIs all reside in membranes and are substrates for kinases, phosphatases and lipases.

In vitro, PI3Ks phosphorylate the 3-hydroxyl group of the inositol ring in three different substrates: phosphatidylinositol (PtdIns), phosphatidylinositol-4-phosphate (PI(4)P) and phosphatidylinositol-4,5-biphosphate (PI(4,5)P2), respectively generating three lipid products, namely phosphatidylinositol 3-monophosphate (PI(3)P), phosphatidylinositol 3,4-bisphosphate (PI(3,4)P2) and phosphatidylinositol 3,4,5-trisphosphate (PI(3,4,5)P3 (see Scheme A below).

Scheme A

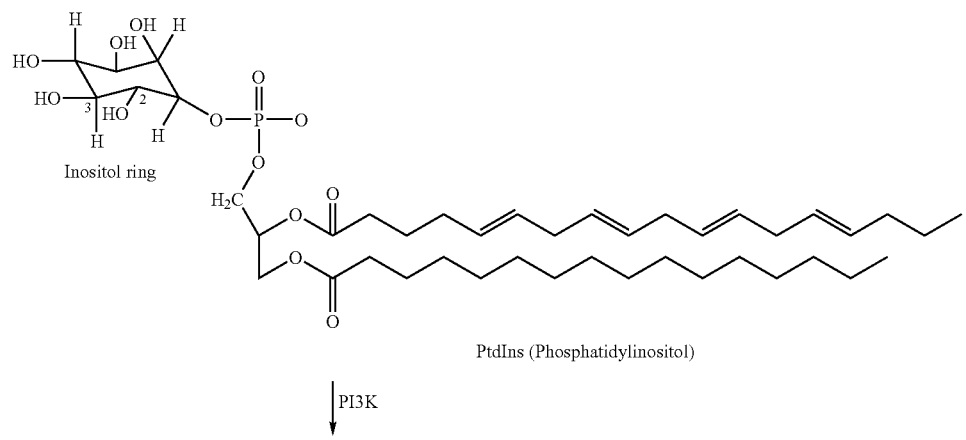

PtdIns (Phosphatidylinositol)

↓ PI3K

-continued

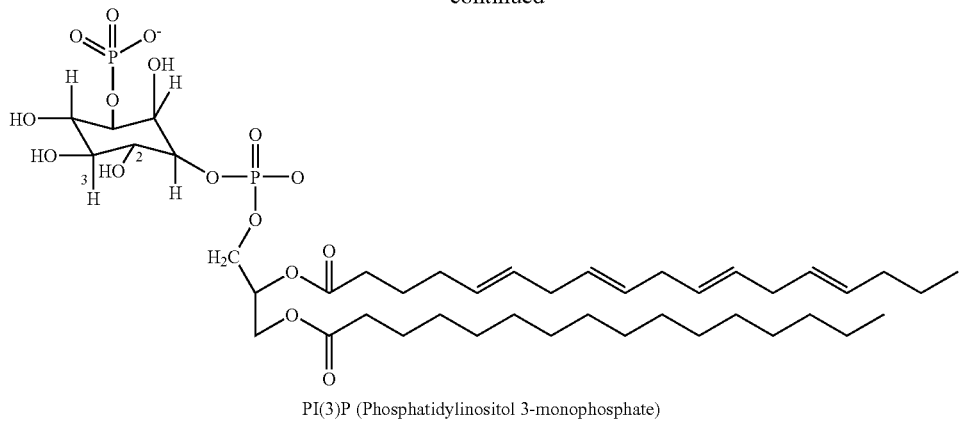

PI(3)P (Phosphatidylinositol 3-monophosphate)

The preferred substrate for Class I PI3Ks is PI(4,5)P$_2$. Class II PIKs have a strong preference for PtdIns as substrate over PI(4)P and PI(4,5)P$_2$. Class III PI3Ks can only use PtdIns as substrate in vivo and are likely to be responsible for the generation of most PI(3)P in cells (Vanhaesebroeck et al., 2001, above).

The phosphoinositides intracellular signaling pathway begins with the binding of a signaling molecule (extracellular ligands, stimuli, receptor dimerization, transactivation by heterologous receptor (e.g. receptor tyrosine kinase)) to a G-protein linked transmembrane receptor integrated into the plasma membrane resulting in the activation of PI3Ks.

Once activated, PI3Ks convert the membrane phospholipid PI(4,5)P$_2$ into PI(3,4,5)P$_3$ which in turn can be further converted into another 3' phosphorylated form of phosphoinositides by 5'-specific phosphoinositide phosphatases, thus PI3K enzymatic activity results either directly or indirectly in the generation of two 3'-phosphoinositide sub-types that function as second messengers in intra-cellular signal transduction (Toker et al., 2002, Cell Mol. Life. Sci. 59(5) 761-79).

The role as second messengers of phosphorylated products of PtdIns act is involved in a variety of signal transduction pathways, including those essential to cell proliferation, cell differentiation, cell growth, cell size, cell survival, apoptosis, adhesion, cell motility, cell migration, chemotaxis, invasion, cytoskeleton rearrangement, cell shape changes, vesicle trafficking and metabolic pathway (Stein, 2000, Mol. Med. Today 6(9) 347-57). Chemotaxis—the directed movement of cells toward a concentration gradient of chemical attractants, also called chamomiles is involved in many important diseases such as inflammation/auto-immunity, neurodegeneration, angiogenesis, invasion/metastasis and wound healing (Wyman et al., 2000, Immunol Today 21(6) 260-4; Hirsch et al., 2000, Science 287(5455) 1049-53; Hirsch et al., 2001, FASEB J 15(11) 2019-21 and Gerard et al., 2001, Nat Immunol. 2(2) 108-15).

PI3-kinase activation, is therefore believed to be involved in a range of cellular responses including cell growth, differentiation and apoptosis (Parker et al., 1995, Current Biology, 5, 577-99; Yao et al., 1995, Science, 267, 2003-05).

Recent biochemical studies revealed that, Class I PI3Ks (e.g. Class IB isoform PI3Kγ) are dual-specific kinase enzymes, i.e. they display both lipid kinase activity (phosphorylation of phospho-inositides) as well as protein kinase activity, as they are able to induce the phosphorylation of other protein as substrates, including auto-phosphorylation as intra-molecular regulatory mechanism.

PI3Ks appear to be involved in a number of aspects of leukocyte activation. A p85-associated PI3-kinase activity has been shown to physically associate with the cytoplasmic domain of CD28, which is an important co-stimulatory molecule for the activation of T-cells in response to antigen. These effects are linked to increases in the transcription of a number of genes including interleukin-2 (IL-2), an important T cell growth factor (Fraser et al., 1991, Science, 251, 313-16). Mutation of CD28 such that it can longer interact with PI3-kinase leads to a failure to initiate IL-2 production, suggesting a critical role for PI3-kinase in T cell activation.

Cellular processes in which PI3Ks play an essential role include suppression of apoptosis, reorganization of the actin skeleton, cardiac myocyte growth, glycogen synthase stimulation by insulin, TNFα-mediated neutrophil priming and superoxide generation, and leukocyte migration and adhesion to endothelial cells.

PI3Kγ has been identified as a mediator of G beta-gamma-dependent regulation of JNK activity wherein G beta-gamma are subunits of heterotrimeric G proteins.

Recently, it has been described that PI3Kγ relays inflammatory signals through various G(I)-coupled receptors (Laffargue et al., 2002, Immunity 16(3) 441-51) and its central to mast cell function, stimuli in context of leukocytes, immunology includes cytokines, chamomiles, adenosines, antibodies, integrins, aggregation factors, growth factors, viruses or hormones for example (Lawlor et al., 2001, J. Cell Sci., 114 (Pt 16) 2903-1).

Specific inhibitors against individual members of a family of enzymes provide valuable tools for deciphering functions of each enzyme.

Two compounds, LY294002 and wortmannin (cf.hereinafter), have been widely used as PI3-kinase inhibitors. These compounds are non-specific PI3K inhibitors, as they do not distinguish among the four members of Class I PI3-kinases.

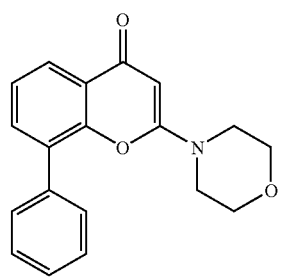

LY 294002

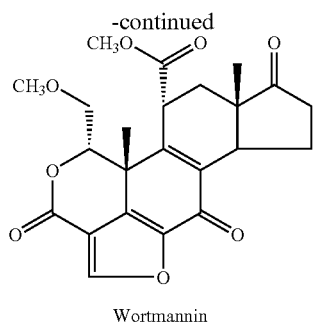

Wortmannin

IC$_{50}$ values of wortmannin against each of the various Class I PI3-kinases are in the range of 1-10 nM and IC$_{50}$ values for LY294002 against each of these PI3-kinases are about 15-20 µM (Fruman et al., 1998, *Ann. Rev. Biochem.*, 67, 481-507), also 5-10 mM on CK2 protein kinase and some inhibitory activity on phospholipases.

Wortmannin is a fungal metabolite which irreversibly inhibits PI3K activity by binding covalently to the catalytic domain of this enzyme. Inhibition of PI3K activity by wortmannin eliminates the subsequent cellular response to the extracellular factor (Thelen et al., 1994, *Proc. Natl. Acad. Sci. USA*, 91, 4960-64). Experiments with wortmannin, show that PI3K activity in cells of hematopoietic lineage, particularly neutrophils, monocytes, and other types of leukocytes, is involved in many of the non-memory immune response associated with acute and chronic inflammation.

Based on studies using wortmannin, there is evidence that PI3-kinase function is also required for some aspects of leukocyte signaling through G-protein coupled receptors (Thelen et al., 1994). Moreover, it has been shown that wortmannin and LY294002 block neutrophil migration and superoxide release. However, in as much as these compounds do not distinguish among the various isoforms of Pl3K, it remains unclear which particular PI3K isoform or isoforms are involved in these phenomena.

Some results have indicated that PI3K inhibitors, for example, LY294002, can increase the in vivo antitumor activity of certain cytotoxic agents (e.g. paclitaxel) (Grant, 2003, *Current Drugs*, 6(10), 946-948).

Recently, thiazole derivatives have been recently developed as PI3K inhibitors (WO 2005/021519; WO 04/078754 and WO 04096797).

WO 2005/021519 discloses thiazole derivatives of the following structure:

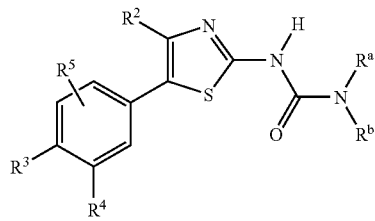

WO 04/078754 discloses thiazole derivatives of the following structure:

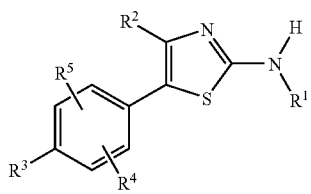

WO 04096797 discloses thiazole derivatives of the following structure:

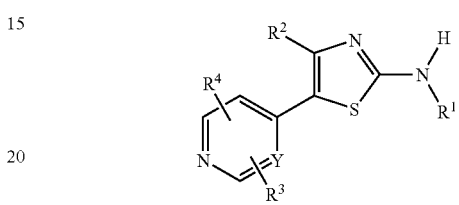

The high relevance of the PI3K pathway in some widely spread diseases stresses the need to develop inhibitors, including selective inhibitors, of PIKs.

SUMMARY OF THE INVENTION

One embodiment of the present invention provides substances which are suitable for the treatment and/or prevention of disorders related to phosphoinositide-3-kinases, PI3Ks.

Another embodiment of the present invention provides substances which are suitable for the treatment and/or prevention of auto-immune and/or inflammatory disorders.

Another embodiment of the present invention provides substances which are suitable for the treatment and/or prevention of cardiovascular diseases.

Another embodiment of the present invention provides substances which are suitable for the treatment and/or prevention of neurodegenerative disorders.

Another embodiment of the present invention provides substances which are suitable for the treatment and/or prevention of a disorder selected from bacterial and viral infections, allergy, asthma, pancreatitis, multi-organ failure, kidney diseases, platelet aggregation, cancer, transplantation, sperm motility, erythrocyte deficiency, graft rejection, lung injuries, respiratory diseases and ischemic conditions.

Another embodiment of the present invention provides chemical compounds which are able to modulate, especially inhibit the activity or function of phosphoinositide-3-kinases, PI3Ks in disease states in mammals, especially in humans.

Another embodiment of the present invention provides a new category of pharmaceutical formulations for the treatment of and/or diseases mediated selected from auto-immune, inflammatory disorders, cardiovascular diseases, neurodegenerative disorders, bacterial and viral infections, allergy, asthma, pancreatitis, multi-organ failure, kidney diseases, platelet aggregation, cancer, transplantation, sperm motility, erythrocyte deficiency, graft rejection, lung injuries, respiratory diseases and ischemic conditions.

Another embodiment of the present invention provides a method for the treatment and/or prevention of disorders selected from auto-immune, inflammatory disorders, cardiovascular diseases, neurodegenerative disorders, bacterial and viral infections, allergy, asthma, pancreatitis, multi-organ failure, kidney diseases, platelet aggregation, cancer, transplantation, sperm motility, erythrocyte deficiency, graft rejection, lung injuries, respiratory diseases and ischemic conditions.

In one embodiment, the invention provides thiazole derivatives of Formula (I):

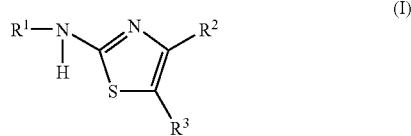

(I)

wherein $R^1$, $R^2$ and $R^3$ are defined in the detailed description below.

In another embodiment, the invention provides a compound according to Formula (I) for use as a medicament.

In another embodiment, the invention provides a use of a compound according to Formula (I) for the preparation of a pharmaceutical composition for the treatment of a disorder selected from auto-immune, inflammatory disorders, cardiovascular diseases, neurodegenerative disorders, bacterial and viral infections, allergy, asthma, pancreatitis, multi-organ failure, kidney diseases, platelet aggregation, cancer, transplantation, sperm motility, erythrocyte deficiency, graft rejection, lung injuries, respiratory diseases and ischemic conditions and other diseases and disorders associated with the phosphoinositide-3-kinases, PI3 Ks, comprising PI3K α and γ.

In another embodiment, the invention provides a pharmaceutical composition comprising at least one a compound according to Formula (I) and a pharmaceutically acceptable carrier, diluent or excipient thereof.

In another embodiment, the invention provides a method for treating a patient suffering from a disorder selected from auto-immune, inflammatory disorders, cardiovascular diseases, neurodegenerative disorders, bacterial and viral infections, allergy, asthma, pancreatitis, multi-organ failure, kidney diseases, platelet aggregation, cancer, transplantation, sperm motility, erythrocyte deficiency, graft rejection, lung injuries, respiratory diseases and ischemic conditions and other diseases and disorders associated with the phosphoinositide-3-kinases, PI3Ks. The method comprises administering a compound according to Formula (I).

In another embodiment, the invention provides compounds according to Formula (P2).

DETAILED DESCRIPTION OF THE INVENTION

The following paragraphs provide definitions of the various chemical moieties that make up the compounds according to the invention and are intended to apply uniformly through-out the specification and claims unless an otherwise expressly set out definition provides a broader definition.

"$C_1$-$C_6$-alkyl" refers to monovalent alkyl groups having 1 to 6 carbon atoms. This term is exemplified by groups such as methyl, ethyl, n-propyl, isopropyl, n-butyl, isobutyl, tert-butyl, n-hexyl and the like. By analogy, "$C_1$-$C_{12}$-alkyl" refers to monovalent alkyl groups having 1 to 12 carbon atoms, including "$C_1$-$C_6$-alkyl" groups and heptyl, octyl, nonyl, decanoyl, undecanoyl and dodecanoyl groups and "$C_1$-$C_{10}$-alkyl" refers to monovalent alkyl groups having 1 to 10 carbon atoms, "$C_1$-$C_8$-alkyl" refers to monovalent alkyl groups having 1 to 8 carbon atoms and "$C_1$-$C_5$-alkyl" refers to monovalent alkyl groups having 1 to 5 carbon atoms.

"Heteroalkyl" refers to $C_1$-$C_{12}$-alkyl, preferably $C_1$-$C_6$-alkyl, wherein at least one carbon has been replaced by a heteroatom selected from O, N or S, including 2-methoxy ethyl.

"Aryl" refers to an unsaturated aromatic carbocyclic group of from 6 to 14 carbon atoms having a single ring (e.g., phenyl) or multiple condensed rings (e.g., naphthyl). Aryl include phenyl, naphthyl, phenantrenyl and the like.

"$C_1$-$C_6$-alkyl aryl" refers to aryl groups having a $C_1$-$C_6$-alkyl substituent, including methyl phenyl, ethyl phenyl and the like.

"Aryl $C_1$-$C_6$-alkyl" refers to $C_1$-$C_6$-alkyl groups having an aryl substituent, including 3-phenylpropanoyl, benzyl and the like.

"Heteroaryl" refers to a monocyclic heteroaromatic, or a bicyclic or a tricyclic fused-ring heteroaromatic group. Particular examples of heteroaromatic groups include optionally substituted pyridyl, pyrrolyl, pyrimidinyl, furyl, thienyl, imidazolyl, oxazolyl, isoxazolyl, thiazolyl, isothiazolyl, pyrazolyl, 1,2,3-triazolyl, 1,2,4-triazolyl, 1,2,3-oxadiazolyl, 1,2,4-oxadiazolyl, 1,2,5-oxadiazolyl, 1,3,4-oxadiazolyl, 1,3,4-triazinyl, 1,2,3-triazinyl, benzofuryl, [2,3-dihydro]benzofuryl, isobenzofuryl, benzothienyl, benzotriazolyl, isobenzothienyl, indolyl, isoindolyl, 3H-indolyl, benzimidazolyl, imidazo[1,2-a]pyridyl, benzothiazolyl, benzoxa-zolyl, quinolizinyl, quinazolinyl, pthalazinyl, quinoxalinyl, cinnolinyl, napthyridinyl, pyrido[3,4-b]pyridyl, pyrido[3,2-b]pyridyl, pyrido[4,3-b]pyridyl, quinolyl, isoquinolyl, tetrazolyl, 5,6,7,8-tetrahydroquinolyl, 5,6,7,8-tetrahydroisoquinolyl, purinyl, pteridinyl, carbazolyl, xanthenyl or benzoquinolyl.

"$C_1$-$C_6$-alkyl heteroaryl" refers to heteroaryl groups having a $C_1$-$C_6$-alkyl substituent, including methyl furyl and the like.

"Heteroaryl $C_1$-$C_6$-alkyl" refers to $C_1$-$C_6$-alkyl groups having a heteroaryl substituent, including furyl methyl and the like.

"$C_2$-$C_6$-alkenyl" refers to alkenyl groups preferably having from 2 to 6 carbon atoms and having at least 1 or 2 sites of alkenyl unsaturation. Preferable alkenyl groups include ethenyl (—CH=$CH_2$), n-2-propenyl (allyl, —$CH_2$CH=$CH_2$) and the like.

"$C_2$-$C_6$-alkenyl aryl" refers to an aryl groups having a $C_2$-$C_6$-alkenyl substituent, including vinyl phenyl and the like.

"Aryl $C_2$-$C_6$-alkenyl" refers to a $C_2$-$C_6$-alkenyl groups having an aryl substituent, including phenyl vinyl and the like.

"$C_2$-$C_6$-alkenyl heteroaryl" refers to heteroaryl groups having a $C_2$-$C_6$-alkenyl substituent, including vinyl pyridinyl and the like.

"Heteroaryl $C_2$-$C_6$-alkenyl" refers to $C_2$-$C_6$-alkenyl groups having a Heteroaryl substituent, including pyridinyl vinyl and the like.

"$C_2$-$C_6$-alkynyl" refers to alkynyl groups preferably having from 2 to 6 carbon atoms and having at least 1-2 sites of alkynyl unsaturation, preferred alkynyl groups include ethynyl (—C≡CH), propargyl (—$CH_2$C≡CH), and the like.

"$C_3$-$C_8$-cycloalkyl" refers to a saturated carbocyclic group of from 3 to 8 carbon atoms having a single ring (e.g., cyclohexyl) or multiple condensed rings (e.g., norbornyl). $C_3$-$C_8$-cycloalkyl include cyclopentyl, cyclohexyl, norbornyl and the like.

"Heterocycloalkyl" refers to a $C_3$-$C_8$-cycloalkyl group according to the definition above, in which up to 3 carbon atoms are replaced by heteroatoms chosen from the group consisting of O, S, NR, R being defined as hydrogen or methyl. Heterocycloalkyl include pyrrolidine, piperidine, piperazine, morpholine, tetrahydrofurane and the like.

"$C_1$-$C_6$-alkyl cycloalkyl" refers to $C_3$-$C_8$-cycloalkyl groups having a $C_1$-$C_6$-alkyl substituent, including methyl cyclopentyl and the like.

"Cycloalkyl $C_1$-$C_6$-alkyl" refers to $C_1$-$C_6$-alkyl groups having a $C_3$-$C_8$-cycloalkyl substituent, including 3-cyclopentyl propyl and the like.

"$C_1$-$C_6$-alkyl heterocycloalkyl" refers to heterocycloalkyl groups having a $C_1$-$C_6$-alkyl substituent, including 1-methylpiperazine and the like.

"Heterocycloalkyl $C_1$-$C_6$-alkyl" refers to $C_1$-$C_6$-alkyl groups having a heterocycloalkyl substituent, including 4-methyl piperidyl and the like.

"Carboxy" refers to the group —C(O)OH.

"Carboxy $C_1$-$C_6$-alkyl" refers to $C_1$-$C_6$-alkyl groups having an carboxy substituent, including 2-carboxyethyl and the like.

"Acyl" refers to the group —C(O)R where R includes H, "$C_1$-$C_{12}$-alkyl", preferably "$C_1$-$C_6$-alkyl", "aryl", "heteroaryl", "$C_3$-$C_8$-cycloalkyl", "heterocycloalkyl", "aryl $C_1$-$C_6$-alkyl", "heteroaryl $C_1$-$C_6$-alkyl", "$C_3$-$C_8$-cycloalkyl $C_1$-$C_6$-alkyl" or "heterocycloalkyl $C_1$-$C_6$-alkyl".

"Acyl $C_1$-$C_6$-alkyl" to $C_1$-$C_6$-alkyl groups having an acyl substituent, including acetyl, 2-acetylethyl and the like.

"Acyl aryl" refers to aryl groups having an acyl substituent, including 2-acetylphenyl and the like.

"Acyloxy" refers to the group —OC(O)R where R includes H, "$C_1$-$C_6$-alkyl", "$C_2$-$C_6$-alkenyl", "$C_2$-$C_6$-alkynyl", "$C_3$-$C_8$-cycloalkyl", "heterocycloalkyl", "aryl", "heteroaryl", "aryl $C_1$-$C_6$-alkyl" or "heteroaryl $C_1$-$C_6$-alkyl", "aryl $C_2$-$C_6$-alkenyl", "heteroaryl $C_2$-$C_6$-alkenyl", "aryl $C_2$-$C_6$-alkynyl", "heteroaryl $C_2$-$C_6$-alkynyl", "cycloalkyl $C_1$-$C_6$-alkyl", "heterocycloalkyl $C_1$-$C_6$-alkyl".

"Acyloxy $C_1$-$C_6$-alkyl" refers to $C_1$-$C_6$-alkyl groups having an acyloxy substituent, including propionic acid ethyl ester and the like.

"Alkoxy" refers to the group —O—R where R includes "$C_1$-$C_6$-alkyl" or "aryl" or "hetero-aryl" or "aryl $C_1$-$C_6$-alkyl" or "heteroaryl $C_1$-$C_6$-alkyl". Preferred alkoxy groups include for example, methoxy, ethoxy, phenoxy and the like.

"Alkoxy $C_1$-$C_6$-alkyl" refers to alkoxy groups having a $C_1$-$C_6$-alkyl substituent, including methoxy, methoxyethyl and the like.

"Alkoxycarbonyl" refers to the group —C(O)OR where R includes H, "$C_1$-$C_6$-alkyl" or "aryl" or "heteroaryl" or "aryl $C_1$-$C_6$-alkyl" or "heteroaryl $C_1$-$C_6$-alkyl" or "heteroalkyl".

"Alkoxycarbonyl $C_1$-$C_6$-alkyl" refers to $C_1$-$C_5$-alkyl groups having an alkoxycarbonyl substituent, including 2-(benzyloxycarbonyl)ethyl and the like.

"Aminocarbonyl" refers to the group —C(O)NRR' where each R, R' includes independently hydrogen or $C_1$-$C_6$-alkyl or aryl or heteroaryl or "aryl $C_1$-$C_6$-alkyl" or "heteroaryl $C_1$-$C_6$-alkyl", including N-phenyl formamide.

"Aminocarbonyl $C_1$-$C_6$-alkyl" refers to $C_1$-$C_6$-alkyl groups having an aminocarbonyl substituent, including 2-(dimethylaminocarbonyl)ethyl, N-ethyl acetamide, N,N-Diethyl-acetamide and the like.

"Acylamino" refers to the group —NRC(O)R' where each R, R' is independently hydrogen, "$C_1$-$C_6$-alkyl", "$C_2$-$C_6$-alkenyl", "$C_2$-$C_6$-alkynyl", "$C_3$-$C_8$-cycloalkyl", "heterocycloalkyl", "aryl", "heteroaryl", "aryl $C_1$-$C_6$-alkyl" or "heteroaryl $C_1$-$C_6$-alkyl", "aryl $C_2$-$C_6$-alkenyl", "heteroaryl $C_2$-$C_6$-alkenyl", "aryl $C_2$-$C_6$-alkynyl", "heteroaryl $C_2$-$C_6$-alkynyl", "cycloalkyl $C_1$-$C_6$-alkyl", "heterocycloalkyl $C_1$-$C_6$-alkyl".

"Acylamino $C_1$-$C_6$-alkyl" refers to $C_1$-$C_6$-alkyl groups having an acylamino substituent, including 2-(propionylamino)ethyl and the like.

"Ureido" refers to the group —NRC(O)NR'R" where each R, R', R" is independently hydrogen, "$C_1$-$C_6$-alkyl", "$C_2$-$C_6$-alkenyl", "$C_2$-$C_6$-alkynyl", "$C_3$-$C_8$-cycloalkyl", "heterocycloalkyl", "aryl", "heteroaryl", "aryl $C_1$-$C_6$-alkyl" or "heteroaryl $C_1$-$C_6$-alkyl", "aryl $C_2$-$C_6$-alkenyl", "heteroaryl $C_2$-$C_6$-alkenyl", "aryl $C_2$-$C_6$-alkynyl", "heteroaryl $C_2$-$C_6$-alkynyl", "cycloalkyl $C_1$-$C_6$-alkyl", "heterocycloalkyl $C_1$-$C_6$-alkyl", and where R' and R", together with the nitrogen atom to which they are attached, can optionally form a 3-8-membered heterocycloalkyl ring.

"Ureido $C_1$-$C_6$-alkyl" refers to $C_1$-$C_6$-alkyl groups having an ureido substituent, including 2-(N-methylureido)ethyl and the like.

"Carbamate" refers to the group —NRC(O)OR' where each R, R' is independently hydrogen, "$C_1$-$C_6$-alkyl", "$C_2$-$C_6$-alkenyl", "$C_2$-$C_6$-alkynyl", "$C_3$-$C_8$-cycloalkyl", "heterocycloalkyl", "aryl", "heteroaryl", "$C_1$-$C_6$-alkyl aryl" or "heteroaryl $C_1$-$C_6$-alkyl", "aryl $C_2$-$C_6$-alkenyl", "heteroaryl $C_2$-$C_6$-alkenyl", "aryl $C_2$-$C_6$-alkynyl", "heteroaryl $C_2$-$C_6$-alkynyl", "cycloalkyl $C_1$-$C_6$-alkyl", "heterocycloalkyl $C_1$-$C_6$-alkyl".

"Amino" refers to the group —NRR' where each R, R' is independently hydrogen or "$C_1$-$C_6$-alkyl" or "aryl" or "heteroaryl" or "$C_1$-$C_6$-alkyl aryl" or "$C_1$-$C_6$-alkyl heteroaryl", or "cycloalkyl", or "heterocycloalkyl", and where R and R', together with the nitrogen atom to which they are attached, can optionally form a 3-8-membered heterocycloalkyl ring.

"Amino $C_1$-$C_6$-alkyl" refers to $C_1$-$C_5$-alkyl groups having an amino substituent, including 2-(1-pyrrolidinyl)ethyl and the like.

"Ammonium" refers to a positively charged group —N$^+$R'R", where each R, R', R" is independently "$C_1$-$C_6$-alkyl" or "$C_1$-$C_6$-alkyl aryl" or "$C_1$-$C_6$-alkyl heteroaryl", or "cycloalkyl", or "heterocycloalkyl", and where R and R', together with the nitrogen atom to which they are attached, can optionally form a 3-8-membered heterocycloalkyl ring.

"Ammonium $C_1$-$C_6$-alkyl" refers to $C_1$-$C_6$-alkyl groups having an ammonium substituent, including 1-ethylpyrrolidinium and the like.

"Halogen" refers to fluoro, chloro, bromo and iodo atoms.

"Sulfonyloxy" refers to a group —OSO$_2$—R wherein R is selected from H, "$C_1$-$C_6$-alkyl", "$C_1$-$C_6$-alkyl" substituted with halogens, e.g., an —OSO$_2$—CF$_3$ group, "$C_2$-$C_6$-alkenyl", "$C_2$-$C_6$-alkynyl", "$C_3$-$C_8$-cycloalkyl", "heterocycloalkyl", "aryl", "heteroaryl", "aryl $C_1$-$C_6$-alkyl" or "heteroaryl $C_1$-$C_6$-alkyl", "aryl $C_2$-$C_6$-alkenyl", "heteroaryl $C_2$-$C_6$-alkenyl", "aryl $C_2$-$C_6$-alkynyl", "heteroaryl $C_2$-$C_6$-alkynyl", "cycloalkyl $C_1$-$C_6$-alkyl", "heterocycloalkyl $C_1$-$C_6$-alkyl".

"Sulfonyloxy $C_1$-$C_6$-alkyl" refers to $C_1$-$C_6$-alkyl groups having a sulfonyloxy substituent, including 2-(methylsulfonyloxy)ethyl and the like.

"Sulfonyl" refers to group "—SO$_2$—R" wherein R is selected from H, "aryl", "heteroaryl", "$C_1$-$C_6$-alkyl", "$C_1$-$C_6$-alkyl" substituted with halogens, e.g., an —SO$_2$—CF$_3$ group, "$C_2$-$C_6$-alkenyl", "$C_2$-$C_6$-alkynyl", "$C_3$-$C_8$-cycloalkyl", "heterocycloalkyl", "aryl", "heteroaryl", "aryl $C_1$-$C_6$-alkyl" or "heteroaryl $C_1$-$C_6$-alkyl", "aryl $C_2$-$C_6$-alkenyl", "heteroaryl $C_2$-$C_6$-alkenyl", "aryl $C_2$-$C_6$-alkynyl", "heteroaryl $C_2$-$C_6$-alkynyl", "cycloalkyl $C_1$-$C_6$-alkyl", "heterocycloalkyl $C_1$-$C_6$-alkyl".

"Sulfonyl $C_1$-$C_6$-alkyl" refers to $C_1$-$C_5$-alkyl groups having a sulfonyl substituent, including 2-(methylsulfonyl)ethyl and the like.

"Sulfinyl" refers to a group "—S(O)—R" wherein R is selected from H, "$C_1$-$C_6$-alkyl", "$C_1$-$C_6$-alkyl" substituted with halogens, e.g., a —SO—$CF_3$ group, "$C_2$-$C_6$-alkenyl", "$C_2$-$C_6$-alkynyl", "$C_3$-$C_8$-cycloalkyl", "heterocycloalkyl", "aryl", "heteroaryl", "aryl $C_1$-$C_6$-alkyl" or "heteroaryl $C_1$-$C_6$-alkyl", "aryl $C_2$-$C_6$-alkenyl", "heteroaryl $C_2$-$C_6$-alkenyl", "aryl $C_2$-$C_6$-alkynyl", "heteroaryl $C_2$-$C_6$-alkynyl", "cycloalkyl $C_1$-$C_6$-alkyl", "heterocycloalkyl $C_1$-$C_6$-alkyl".

"Sulfinyl $C_1$-$C_6$-alkyl" refers to $C_1$-$C_6$-alkyl groups having a sulfinyl substituent, including 2-(methylsulfinyl)ethyl and the like.

"Sulfanyl" refers to groups —S—R where R includes H, "$C_1$-$C_6$-alkyl", "$C_1$-$C_6$-alkyl" substituted with halogens, e.g., a —SO—$CF_3$ group, "$C_2$-$C_6$-alkenyl", "$C_2$-$C_6$-alkynyl", "$C_3$-$C_8$-cycloalkyl", "heterocycloalkyl", "aryl", "heteroaryl", "aryl $C_1$-$C_6$-alkyl" or "heteroaryl $C_1$-$C_6$-alkyl", "aryl $C_2$-$C_6$-alkenyl", "heteroaryl $C_2$-$C_6$-alkenyl", "aryl $C_2$-$C_6$-alkynyl", "alkynylheteroaryl $C_2$-$C_6$,", "cycloalkyl $C_1$-$C_6$-alkyl", "heterocycloalkyl $C_1$-$C_6$-alkyl". Preferred sulfanyl groups include methylsulfanyl, ethylsulfanyl, and the like.

"Sulfanyl $C_1$-$C_6$-alkyl" refers to $C_1$-$C_5$-alkyl groups having a sulfanyl substituent, including 2-(ethylsulfanyl)ethyl and the like.

"Sulfonylamino" refers to a group —$NRSO_2$—R' where each R, R' includes independently hydrogen, "$C_1$-$C_6$-alkyl", "$C_2$-$C_6$-alkenyl", "$C_2$-$C_6$-alkynyl", "$C_3$-$C_8$-cycloalkyl", "heterocycloalkyl", "aryl", "heteroaryl", "aryl $C_1$-$C_6$-alkyl" or "heteroaryl $C_1$-$C_6$-alkyl", "aryl $C_2$-$C_6$-alkenyl", "heteroaryl $C_2$-$C_6$-alkenyl", "aryl $C_2$-$C_6$-alkynyl", "heteroaryl $C_2$-$C_6$-alkynyl", "cycloalkyl $C_1$-$C_6$-alkyl", "heterocycloalkyl $C_1$-$C_6$-alkyl".

"Sulfonylamino $C_1$-$C_6$-alkyl" refers to $C_1$-$C_6$-alkyl groups having a sulfonylamino substituent, including 2-(ethylsulfonylamino)ethyl and the like.

"Aminosulfonyl" refers to a group —$SO_2$—NRR' where each R, R' includes independently hydrogen, "$C_1$-$C_6$-alkyl", "$C_2$-$C_6$-alkenyl", "$C_2$-$C_6$-alkynyl", "$C_3$-$C_8$-cycloalkyl", "heterocycloalkyl", "aryl", "heteroaryl", "aryl $C_1$-$C_6$-alkyl" or "heteroaryl $C_1$-$C_6$-alkyl", "aryl $C_2$-$C_6$-alkenyl", "heteroaryl $C_2$-$C_6$-alkenyl", "aryl $C_2$-$C_6$-alkynyl", "heteroaryl $C_2$-$C_6$-alkynyl", "cycloalkyl $C_1$-$C_6$-alkyl", "heterocycloalkyl $C_1$-$C_6$-alkyl".

"Aminosulfonyl $C_1$-$C_6$-alkyl" refers to $C_1$-$C_6$-alkyl groups having an aminosulfonyl substituent, including 2-(cyclohexylaminosulfonyl)ethyl and the like.

"Substituted or unsubstituted": Unless otherwise constrained by the definition of the individual substituent, the above set out groups, like "alkenyl", "alkynyl", "aryl", "heteroaryl", "cycloalkyl", "heterocycloalkyl" etc. groups can optionally be substituted with from 1 to 5 substituents selected from the group consisting of "$C_1$-$C_6$-alkyl", "$C_2$-$C_6$-alkenyl", "$C_2$-$C_6$-alkynyl", "cycloalkyl", "heterocycloalkyl", "$C_1$-$C_6$-alkyl aryl", "$C_1$-$C_6$-alkyl heteroaryl", "$C_1$-$C_6$-alkyl cycloalkyl", "$C_1$-$C_6$-alkyl heterocycloalkyl", "amino", "ammonium", "acyl", "acyloxy", "acylamino", "aminocarbonyl", "alkoxycarbonyl", "ureido", "aryl", "carbamate", "heteroaryl", "sulfinyl", "sulfonyl", "alkoxy", "sulfanyl", "halogen", "carboxy", trihalomethyl, cyano, hydroxy, mercapto, nitro, and the like.

"Substituted" refers to groups substituted with from 1 to 5 substituents selected from the group consisting of "$C_1$-$C_6$-alkyl", "$C_2$-$C_6$-alkenyl", "$C_2$-$C_6$-alkynyl", "cycloalkyl", "heterocycloalkyl", "$C_1$-$C_6$-alkyl aryl", "$C_1$-$C_6$-alkyl heteroaryl", "$C_1$-$C_6$-alkyl cycloalkyl", "$C_1$-$C_6$-alkyl heterocycloalkyl", "amino", "aminosulfonyl", "ammonium", "acyl amino", "amino carbonyl", "aryl", "heteroaryl", "sulfinyl", "sulfonyl", "alkoxy", "alkoxy carbonyl", "carbamate", "sulfanyl", "halogen", trihalomethyl, cyano, hydroxy, mercapto, nitro, and the like "Pharmaceutically acceptable salts or complexes" refers to salts or complexes of the below-identified compounds of Formula (I) that retain the desired biological activity.

Examples of such salts include, but are not restricted to acid addition salts formed with inorganic acids (e.g., hydrochloric acid, hydrobromic acid, sulfuric acid, phosphoric acid, nitric acid, and the like), and salts formed with organic acids such as acetic acid, oxalic acid, tartaric acid, succinic acid, malic acid, fumaric acid, maleic acid, ascorbic acid, benzoic acid, tannic acid, pamoic acid, alginic acid, polyglutamic acid, naphthalene sulfonic acid, naphthalene disulfonic acid, and poly-galacturonic acid. Said compounds can also be administered as pharmaceutically acceptable quaternary salts known by a person skilled in the art, which specifically include the quarternary ammonium salt of the formula —NR, R', R"$^+$Z$^-$, wherein R, R', R" is independently hydrogen, alkyl, or benzyl, $C_1$-$C_6$-alkyl, $C_2$-$C_6$-alkenyl, $C_2$-$C_6$-alkynyl, $C_1$-$C_6$-alkyl aryl, $C_1$-$C_6$-alkyl heteroaryl, cycloalkyl, heterocycloalkyl, and Z is a counterion, including chloride, bromide, iodide, —O-alkyl, toluenesulfonate, methylsulfonate, sulfonate, phosphate, or carboxylate (such as benzoate, succinate, acetate, glycolate, maleate, malate, fumarate, citrate, tartrate, ascorbate, cinnamoate, mandeloate, and diphenylacetate).

"Pharmaceutically active derivative" refers to any compound that upon administration to the recipient, is capable of providing directly or indirectly, the activity disclosed herein. The term "indirectly" also encompasses prodrugs which may be converted to the active form of the drug via endogenous enzymes or metabolism.

It has now been found that compounds of the present invention are modulators of the Phosphatoinositides 3-kinases (PI3Ks), comprising PI3K α and γ. When the phosphatoinositides 3-kinase (PI3K) enzyme is inhibited by the compounds of the present invention, PI3K is unable to exert its enzymatic, biological and/or pharmacological effects.

The compounds of the present invention are therefore useful in the treatment and prevention of autoimmune disorders and/or inflammatory diseases, cardiovascular diseases, neurodegenerative diseases, bacterial or viral infections, allergy, asthma, pancreatitis, multi-organ failure, kidney diseases, platelet aggregation, cancer, transplantation, sperm motility, erythrocyte deficiency, graft rejection or lung injuries.

General Formula (I) according to the present invention also comprises its tautomers, its geometrical isomers, its optically active forms as enantiomers, diastereomers and its racemate forms, as well as pharmaceutically acceptable salts thereof. Preferred pharmaceutically acceptable salts of the Formula (I) are acid addition salts formed with pharmaceutically acceptable acids like hydrochloride, hydrobromide, sulfate or bisulfate, phosphate or hydrogen phosphate, acetate, benzoate, succinate, fumarate, maleate, lactate, citrate, tartrate, gluconate, methanesulfonate, benzenesulfonate, and para-toluenesulfonate salts.

The compounds according to Formula (I) are suitable for the modulation, notably the inhibition of the activity of phosphatoinositides 3-kinases (PI3K). It is therefore believed that the compounds of the present invention are also particularly useful for the treatment and/or prevention of disorders, which are mediated by PI3Ks, particularly PI3K α and/or PI3K γ. Said treatment involves the modulation—notably the inhibition or the down regulation—of the phosphatoinositides 3-kinases.

The compounds according to Formula (I) are suitable for use as a medicament.

One embodiment of the present invention provides thiazole derivatives of Formula (I):

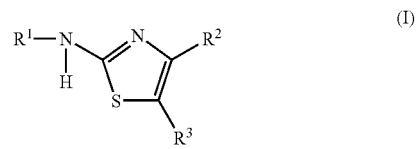

wherein $R^1$ is selected from optionally substituted aryl, optionally substituted heteroaryl, optionally substituted cycloalkyl, optionally substituted heterocycloalkyl and optionally substituted acyl, including acetyl;

$R^2$ is selected from H; halogen; optionally substituted $C_1$-$C_6$-alkyl, including methyl; optionally substituted $C_2$-$C_6$-alkenyl and optionally substituted $C_2$-$C_6$-alkynyl;

$R^3$ is selected from the following thienyl groups:

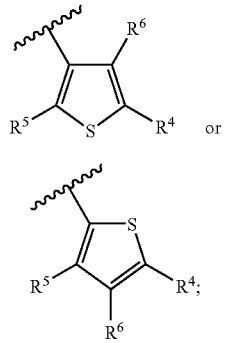

T1 or

T2

$R^4$ is selected from H, optionally substituted $C_1$-$C_6$-alkyl, including optionally substituted amino $C_1$-$C_6$-alkyl such as allylamino methyl (e.g. (5-allylamino)methyl), hydroxymethyl, hydroxyimino methyl and cyano; optionally substituted $C_2$-$C_6$-alkenyl; optionally substituted $C_2$-$C_6$-alkynyl; optionally substituted alkoxycarbonyl, including acetyl;

optionally substituted sulfonyl, including optionally substituted heterocycle sulfonyl such as optionally substituted piperidin sulfonyl (e.g. (3-hydroxypiperidin-1-yl)sulfonyl, (4-hydroxypiperidin-1-yl)sulfonyl), optionally substituted morpholin sulfonyl (morpholin-4-yl sulfonyl) and optionally substituted 8-(1,4-Dioxa-8-azaspiro[4.5]decane)sulfonyl, optionally substituted amino sulfonyl (e.g. (2-hydroxyethyl) amino sulfonyl, allylamino sulfonyl, amino sulfonyl); and optionally substituted acyl, including formyl, carboxylic acid, carboxylic acid alkyl ester (e.g. carboxylic acid methyl ester), optionally substituted morpholine carbonyl (e.g. morpholin-4-yl carbonyl), optionally substituted piperidine carbonyl (e.g. 4-hydroxypiperidin- 1 -yl carbonyl, 3-hydroxypiperidin-1-yl carbonyl);

In still another embodiment according to the invention, the compounds of Formula (I) are useful for the treatment and/or prophylaxis of chronic obstructive pulmonary disease, anaphylactic $R^5$ and $R^6$ are independently selected from H, optionally substituted $C_1$-$C_6$-alkyl, optionally substituted $C_2$-$C_6$-alkenyl, optionally substituted $C_2$-$C_6$-alkynyl and halogen;

as well as its geometrical isomers, its optically active forms as enantiomers, diastereomers and its racemate forms, as well as pharmaceutically acceptable salts thereof.

Another embodiment of the present invention, the invention provides thiazole derivatives of Formula (I) wherein $R^1$ is optionally substituted acyl.

Another embodiment of the present invention provides thiazole derivatives of Formula (I) wherein $R^2$ is methyl.

Another embodiment of the present invention provides thiazole derivatives of Formula (I) wherein $R^3$ is a thienyl T1.

Another embodiment of the present invention provides thiazole derivatives of Formula (I) wherein $R^3$ is a thienyl T2.

Another embodiment of the present invention provides thiazole derivatives of Formula (I) wherein $R^4$ is selected from H, optionally substituted $C_1$-$C_6$-alkyl, optionally substituted $C_2$-$C_6$-alkenyl and optionally substituted $C_2$-$C_6$-alkynyl.

Another embodiment of the present invention provides thiazole derivatives of Formula (I) wherein $R^4$ is optionally substituted sulfonyl.

Another embodiment of the present invention provides thiazole derivatives of Formula (I) wherein $R^4$ is optionally substituted acyl and optionally substituted alkoxycarbonyl.

Another embodiment of the present invention provides thiazole derivatives of Formula (I) wherein $R^5$ and $R^6$ are H.

Compounds of the present invention include in particular those of the group consisting of:

| Example N° | Name |
|---|---|
| 1 | N-[5-(5-formyl-2-thienyl)-4-methyl-1,3-thiazol-2-yl]acetamide; |
| 2 | N-(5-{5-[(allylamino)methyl]-2-thienyl}-4-methyl-1,3-thiazol-2-yl)acetamide; |
| 3 | N-{5-[5-(hydroxymethyl)-2-thienyl]-4-methyl-1,3-thiazol-2-yl}acetamide; |
| 4 | 5-[2-(acetylamino)-4-methyl-1,3-thiazol-5-yl]thiophene-2-carboxylic acid; |
| 5 | N-{4-methyl-5-[5-(morpholin-4-ylcarbonyl)-2-thienyl]-1,3-thiazol-2-yl} acetamide; |
| 6 | N-[4-methyl-5-(2-thienyl)-1,3-thiazol-2-yl]acetamide; |
| 7 | N-(5-{5-[(4-hydroxypiperidin-1-yl)carbonyl]-2-thienyl}-4-methyl-1,3-thiazol-2-yl)acetamide; |
| 8 | N-(5-{5-[(3-hydroxypiperidin-1-yl)carbonyl]-2-thienyl}-4-methyl-1,3-thiazol-2-yl)acetamide; |
| 9 | N-(5-{5-[(3-hydroxypiperidin-1-yl)sulfonyl]-2-thienyl}-4-methyl-1,3-thiazol-2-yl)acetamide; |
| 10 | N-(5-{5-[(4-hydroxypiperidin-1-yl)sulfonyl]-2-thienyl}-4-methyl-1,3-thiazol-2-yl)acetamide; |
| 11 | N-[5-(5-{[(2-hydroxyethyl)amino]sulfonyl}-2-thienyl)-4-methyl-1,3-thiazol-2-yl]acetamide; |
| 12 | N-(5-{5-[(allylamino)sulfonyl]-2-thienyl}-4-methyl-1,3-thiazol-2-yl)acetamide; |
| 13 | N-{4-methyl-5-[5-(morpholin-4-ylsulfonyl)-2-thienyl]-1,3-thiazol-2-yl} acetamide; |
| 14 | N-(5-{5-[(E)-(hydroxyimino)methyl]-2-thienyl}-4-methyl-1,3-thiazol-2-yl) acetamide; |
| 15 | N-[5-(5-cyano-2-thienyl)-4-methyl-1,3-thiazol-2-yl]acetamide; |
| 16 | Methyl 5-[2-(acetylamino)-4-methyl-1,3-thiazol-5-yl]thiophene-2-carboxylate; |
| 17 | N-{5-[5-(aminosulfonyl)-2-thienyl]-4-methyl-1,3-thiazol-2-yl}acetamide; |
| 18 | N-{5-[5-(1,4-dioxa-8-azaspiro[4.5]dec-8-ylsulfonyl)-2-thienyl]-4-methyl-1,3-thiazol-2-yl}acetamide; |
| 19 | _N-[4-methyl-5-(3-thienyl)-1,3-thiazol-2-yl]acetamide. |

The compounds of the present invention are useful as medicaments. They may be used for the preparation of a medicament for the prophylaxis and/or treatment of autoimmune disorders and/or inflammatory diseases, cardiovascular diseases, neurodegenerative diseases, bacterial or viral infections, kidney diseases, platelet aggregation, cancer, transplantation, erythrocyte deficiency, graft rejection or lung injuries.

In one embodiment, the compounds of Formula (I) are useful for the treatment and/or prophylaxis of autoimmune diseases or inflammatory diseases such as multiple sclerosis, psoriasis, rheumatoid arthritis, systemic lupus erythematosis, inflammatory bowel disease, lung inflammation, thrombosis or brain infection/inflammation such as meningitis or encephalitis.

In another embodiment, the compounds of Formula (I) are useful for the treatment and/or prophylaxis of neurodegenerative diseases including Alzheimer's disease, Huntington's disease, CNS trauma, stroke or ischemic conditions.

In still a further embodiment according to the invention, the compounds of Formula (I) are useful for the treatment and/or prophylaxis of cardiovascular diseases such as atherosclerosis, heart hypertrophy, cardiac myocyte dysfunction, elevated blood pressure or vasoconstriction.

In still a further embodiment according to the invention, the compounds of Formula (I) are useful for the treatment and/or prophylaxis of erythrocyte deficiency such as an anaemia, including haemolytic anaemia, aplastic anaemia and pure red cell anaemia. shock, fibrosis, psoriasis, allergic diseases, asthma, stroke or ischemic conditions, ischemia-reperfusion, platelets aggregation/activation, skeletal muscle atrophy/hypertrophy, leukocyte recruitment in cancer tissue, angiogenesis, invasion metastasis, in particular melanoma, Karposi's sarcoma, acute and chronic bacterial and viral infections, sepsis, transplantation, graft rejection, glomerulo sclerosis, glomerulo nephritis, progressive renal fibrosis, endothelial and epithelial injuries in the lung or in general lung airways inflammation.

In another embodiment according to the invention, is provided a process for the preparation of thiazole derivative according to Formula (I), comprising the step of reacting a compound of Formula (P1) with a derivative of Formula (P2) in presence of palladium complexes, such as $Pd(PPh_3)_4$, [1,1'-bis(diphenylphosphino)ferrocene]palladium(II) chloride (Pd (dppf) $Cl_2$), $PdCl_2(PPh_3)_2$, $Pd(OAc)_2$ and a base:

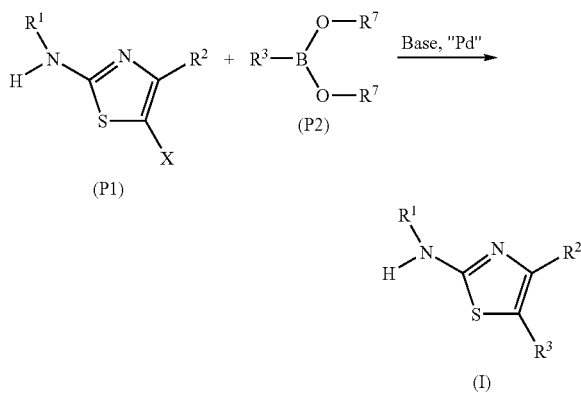

wherein X may be Br or I, $R^7$ may be H, for boronic acid derivatives, or any $C_1$-$C_6$ alkyl or substituted $C_1$-$C_6$ alkyl groups for boronic ester derivatives and wherein the group —$B(OR^7)_2$ can optionally form a heterocycle such as boronic acid pinacol ester.

In a further embodiment according to the invention, is provided a compound according to Formula (P2) which is Methyl 5-(4,4,5,5-tetramethyl-1,3,2-dioxaborolan-2-yl) thiophene-2-carboxylate.

In another embodiment according to the invention, is provided a process for the preparation of thiazole derivative according to Formula (I), comprising the step of reacting a compound of Formula (P1) with a tin derivative of Formula (P3) in presence of palladium complexes, such as $Pd(PPh_3)_4$, [1,1'-bis(diphenylphosphino)ferrocene]palladium(II) chloride (Pd(dppf) $Cl_2$), $PdCl_2(PPh_3)_2$, $Pd(OAc)_2$:

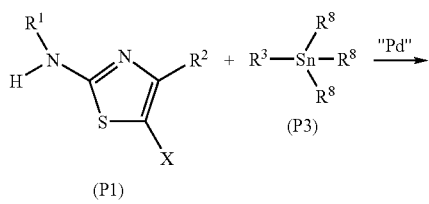

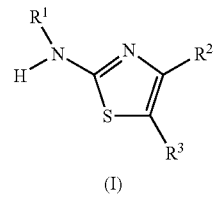

wherein X may be Br or I and $R^8$ is methyl or n-butyl.

The thiazole derivatives exemplified in this invention may be prepared from readily available starting materials using the following general methods and procedures. It will be appreciated that where typical or preferred experimental conditions (i.e. reaction temperatures, time, moles of reagents, solvents etc.) are given, other experimental conditions can also be used unless otherwise stated. Optimum reaction conditions may vary with the particular reactants or solvents used, but such conditions can be determined by the person skilled in the art, using routine optimisation procedures.

When employed as pharmaceuticals, the compounds of the present invention are typically administered in the form of a pharmaceutical composition. Hence, pharmaceutical compositions comprising a compound of Formula (I) and a pharmaceutically acceptable carrier, diluent or excipient therefore are also within the scope of the present invention. A person skilled in the art is aware of a whole variety of such carrier, diluent or excipient compounds suitable to formulate a pharmaceutical composition.

The compounds of the invention, together with a conventionally employed adjuvant, carrier, diluent or excipient may be placed into the form of pharmaceutical compositions and unit dosages thereof, and in such form may be employed as solids, such as tablets or filled capsules, or liquids such as solutions, suspensions, emulsions, elixirs, or capsules filled with the same, all for oral use, or in the form of sterile injectable solutions for parenteral (including subcutaneous use). Such pharmaceutical compositions and unit dosage forms thereof may comprise ingredients in conventional proportions, with or without additional active compounds or principles, and such unit dosage forms may contain any suitable effective amount of the active ingredient commensurate with the intended daily dosage range to be employed.

Pharmaceutical compositions containing thiazole derivatives of this invention can be prepared in a manner well known in the pharmaceutical art and comprise at least one active compound. Generally, the compounds of this invention are administered in a pharmaceutically effective amount. The amount of the compound actually administered will typically be determined by a physician, in the light of the relevant circumstances, including the condition to be treated, the chosen route of administration, the actual compound administered, the age, weight, and response of the individual patient, the severity of the patient's symptoms, and the like.

The pharmaceutical compositions of the present invention can be administered by a variety of routes including oral, rectal, transdermal, subcutaneous, intravenous, intramuscular and intranasal. The compositions for oral administration can take the form of bulk liquid solutions or suspensions, or bulk powders. More commonly, however, the compositions are presented in unit dosage forms to facilitate accurate dosing. The term "unit dosage forms" refers to physically discrete units suitable as unitary dosages for human subjects and other mammals, each unit containing a predetermined quantity of active material calculated to produce the desired therapeutic effect, in association with a suitable pharmaceutical excipient. Typical unit dosage forms include prefilled, premeasured ampoules or syringes of the liquid compositions or pills, tablets, capsules or the like in the case of solid compositions. In such compositions, the thiazole derivative is usually a minor component (from about 0.1 to about 50% by weight or preferably from about 1 to about 40% by weight) with the remainder being various vehicles or carriers and processing aids helpful for forming the desired dosing form.

Liquid forms suitable for oral administration may include a suitable aqueous or nonaqueous vehicle with buffers, suspending and dispensing agents, colorants, flavors and the like. Solid forms may include, for example, any of the following ingredients, or compounds of a similar nature: a binder such as microcrystalline cellulose, gum tragacanth or gelatine; an excipient such as starch or lactose, a disintegrating agent such as alginic acid, Primogel, or corn starch; a lubricant such as magnesium stearate; a glidant such as colloidal silicon dioxide; a sweetening agent such as sucrose or saccharin; or a flavoring agent such as pepper-mint, methyl salicylate, or orange flavoring.

Injectable compositions are typically based upon injectable sterile saline or phosphate-buffered saline or other injectable carriers known in the art. As above mentioned, the thiazole derivatives of Formula (I) in such compositions is typically a minor component, frequently ranging between 0.05 to 10% by weight with the remainder being the injectable carrier and the like.

The above described components for orally administered or injectable compositions are merely representative. Further materials as well as processing techniques and the like are set out in Part 5 of *Remington's Pharmaceutical Sciences*, 20$^{th}$ Edition, 2000, Marck Publishing Company, Easton, Pa., which is incorporated herein by reference.

The compounds of this invention can also be administered in sustained release forms or from sustained release drug delivery systems. A description of representative sustained release materials can also be found in the incorporated materials in *Remington's Pharmaceutical Sciences*.

Synthesis of Compounds of the Invention:

The novel thiazole derivatives according to Formula (I) can be prepared from readily available starting materials by several synthetic approaches, using both solution-phase and solid-phase chemistry protocols (Brummond et al., 1999, *J.O.C.*, 64, 1723-1726). Examples of synthetic pathways for the will be described.

The following abbreviations refer respectively to the definitions below: Å (Angstrom), cm (centimeter), eq (equivalent), h (hour), g (gram), M (molar), MHz (Megahertz), μl (microliter), min (minute), mg (milligram), ml (milliliter), mm (millimeter), mmol (millimole), mM (millimolar), nm (nanometer), rt (room temperature), BSA (Bovine Serum Albumin), CDI (N,N'-carbonyldiimidazole), CMC (Carboxymethyl Cellulose), DCC (dicyclohexyl carbodiimide), DCM (dichloromethane), DIEA (diisopropyl ethylamine), DMF (dimethyl formamide), DMSO (Dimethyl Sulfoxide), EDC (1-(3-dimethylaminopropyl)-3-ethyl-carbo diimidehydro-chloride), HOBt (1-hydroxybenzo triazole), HPLC (High Performance Liquid Chromatography), IHC (immunohistochemistry), Ins1P (D-myo-inositol-1-phosphate), LC (Liquid chromatography), MS (mass spectrometry), NBS (N-bromo succinimide), NIS (N-iodo succinimide), NMR (Nuclear Magnetic Resonance), PBS (Phosphate Buffered Saline), Pd(dppf)Cl$_2$ ([1,1'-bis(diphenylphosphino) ferrocene]palladium(II) chloride complex), PIs (Phosphoinositides), PI3Ks (Phosphoinositide 3-kinases), PI(3)P (Phosphatidylinositol 3-monophosphate), PI(3,4)P$_2$ (Phosphatidylinositol 3,4-bisphosphate), PI(3,4,5)P$_3$ (Phosphatidylinositol 3,4,5-trisphosphate), PI(4)P (Phosphatidylinositol-4-phosphate), PI(4,5)P$_2$ (Phosphatidyl inositol-4,5-biphosphate), PtdIns (Phosphatidylinositol), PyBOP (Benzotriazol-1-yloxy)tripyrrolidino-phosphonium hexafluorophosphate), SPA (Scintillation Proximity Assay), TEA (triethylamine), TFA (trifluoroacetic acid), THF (tetrahydrofuran), TLC (Thin Layer Chromatography), UV (Ultraviolet).

The thiazole derivatives exemplified in this invention may be prepared from readily available starting materials using the following general methods and procedures. It will be appreciated that where typical or preferred experimental conditions (i.e. reaction temperatures, time, moles of reagents, solvents etc.) are given, other experimental conditions can also be used unless otherwise stated. Optimum reaction conditions may vary with the particular reactants or solvents used, but such conditions can be determined by the person skilled in the art, using routine optimisation procedures.

In the process illustrated in the following schemes $R^1$, $R^2$, $R^3$, $R^4$, $R^5$ and $R^6$ as above-defined in the description.

Generally, the thiazole derivatives according to the general Formula (I) could be obtained by several synthetic approaches, using both solution-phase and solid-phase chemistry protocols (Kodomari et al., 2002, *Tetrahedron Lett.*, 43, 1717-1720) either by conventional methods or by microwave-assisted techniques.

The pharmaceutically acceptable cationic salts of compounds of the present invention are readily prepared by reacting the acid forms with an appropriate base, usually one equivalent, in a co-solvent. Typical bases are sodium hydroxide, sodium methoxide, sodium ethoxide, sodium hydride, potassium hydroxide, potassium methoxide, magnesium hydroxide, calcium hydroxide, benzathine, choline, diethanolamine, ethylenediamine, meglumine, benethamine, diethylamine, piperazine and tromethamine. The salt is isolated by concentration to dryness or by addition of a non-solvent. In some cases, salts can be prepared by mixing a solution of the acid with a solution of the cation (sodium ethylhexanoate, magnesium oleate), employing a solvent in which the desired cationic salt precipitates, or can be otherwise isolated by concentration and addition of a non-solvent.

Methods of Preparing Intermediates of Compounds of Formula (I).

Depending on the nature of X, $R^1$, $R^2$, $R^1$, $R^4$, $R^5$ and $R^6$ different synthetic strategies may be selected for the synthesis of compounds of Formula (I).

Compounds of Formula (I) may be obtained by metal catalysed cross-coupling reaction. For instance, they may be obtained by Suzuki coupling reaction between an aryl halide (P1), where X may be Br or I, and a boronic acid or ester (P2), where $R^7$ may be H, for boronic acid derivatives, or any alkyl or substituted alkyl groups for boronic ester derivatives, including optionally —B(OR$^7$)$_2$ forming a cycle such as boronic acid pinacol ester (Scheme 1 below) (Bellina et al., 2004, *Synthesis*, 2419).

Different palladium complexes may be used, such as Pd(PPh$_3$)$_4$, [1,1'-bis(diphenyl phosphino)ferrocene]palladium(II) chloride (Pd(dppf)Cl$_2$), PdCl$_2$(PPh$_3$)$_2$, Pd(OAc)$_2$, with the possible addition of phosphine ligands such as PPh$_3$. Different organic or inorganic bases may be used, such as TEA, DIEA, sodium alcoholate, such as NaOMe or NaOEt, KF, or any carbonate salts, such as K$_2$CO$_3$, Na$_2$CO$_3$, Cs$_2$CO$_3$. The solvent or solvents mixture may be selected between THF, Toluene, Dioxane, MeOH, MeCN, DMF, water, etc. The choice of solvent or solvents mixture may depend on the nature of the base, (P1) and (P2). The resulting reaction mixture may be heated, under inert atmosphere, at different temperatures, with the possible use of microwave action. All the different combinations described above may be used.

Scheme 1

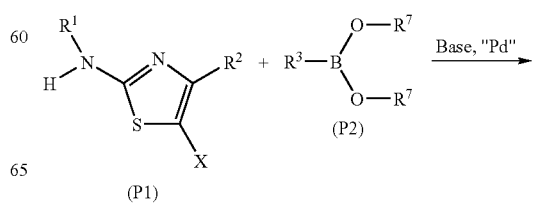

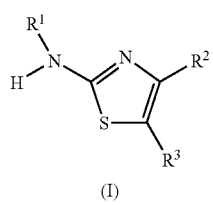

(I)

Stille coupling may be used for the preparation of compounds of Formula (I), involving the reaction between an aryl halide (PI), where X may be Br or I, and a tin reagent (P3), where $R^8$ is methyl or n-butyl (Scheme 2, below). This reaction may be catalysed by different palladium complexes, such as $Pd(PPh_3)_4$, [1,1'-bis(diphenylphosphino)ferrocene]palladium(II) chloride (Pd(dppf) $Cl_2$), $PdCl_2(PPh_3)_2$, $Pd(OAc)_2$, with the possible addition of phosphine ligands, such as $PPh_3$, and chlorine salts, such as LiCl or $ZnCl_2$.

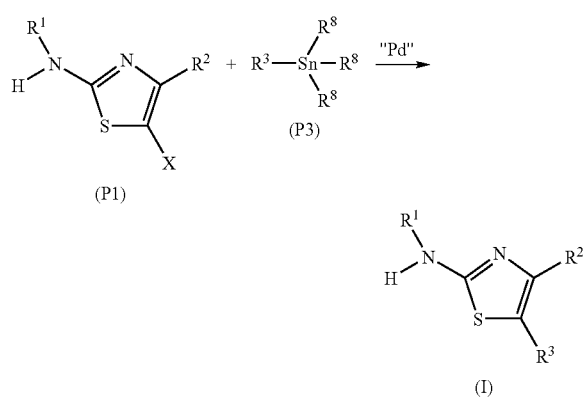

If the above set of metal catalysed cross-coupling reaction conditions is not applicable to obtain compounds according to Formula (I), suitable methods of preparation known by a person skilled in the art should be used.

Compounds of Formula (I) can be converted to alternative compounds of Formula (I), employing suitable interconversion techniques well known by a person skilled in the art. When $R^4$ is H, compounds of Formula (Ia), where $R^3$ may be T1 or T2, may be further functionalised through electrophilic substitutions (Scheme 3 below). For example, chlorosulfonation with chlorosulfonic acid, followed by reaction with $PCl_5$/$POCl_3$ may afford the corresponding sulfonyl chloride (P4).

Intermediate (P4) may further react with an amine, $HNR^9R^{10}$, wherein $R^9$ and $R^{10}$ are selected from H, optionally substituted $C_1$-$C_6$-alkyl (e.g. allyl, 2-hydroxyethyl), optionally —$NR^9R^{10}$ may form a ring, and may be selected from substituted heterocycloalkyl, such as optionally substituted piperidine (e.g. 3-hydroxypiperidin-1-yl, 4-hydroxypiperidin-1-yl), optionally substituted morpholine (e.g. morpholin-4-yl) and optionally substituted 8-(1,4-Dioxa-8-azaspiro[4.5] decane), in the presence of a base, e.g. TEA, DIEA, pyridine, etc, yielding compounds of Formula (Ib) (Compounds of Formula (I) wherein $R^4=SO_2NR^9R^{10}$), an amino sulfonyl as defined above and where $R^3$ may be T1 or T2. Other electrophilic substitutions may be performed on compound of formula (Ia), such as bromination, nitration, formylation, acylation, etc. using conditions known by a person skilled in the art (for example, see *Beaton et al., 1976, J Chem. Soc., Perkin I*, 2355-2363). Compounds of Formula (Ia) may be deprotonated with a suitable base, such as alkyl lithium, affording intermediate (P5), which may further react with an electrophile. For example, reaction of intermediate (P5) with $CO_2$ may afford compounds of Formula (Ic), with $R^3$=T1 or T2 and $R^4$=COOH (*Beaton et al.*, 1976, above).

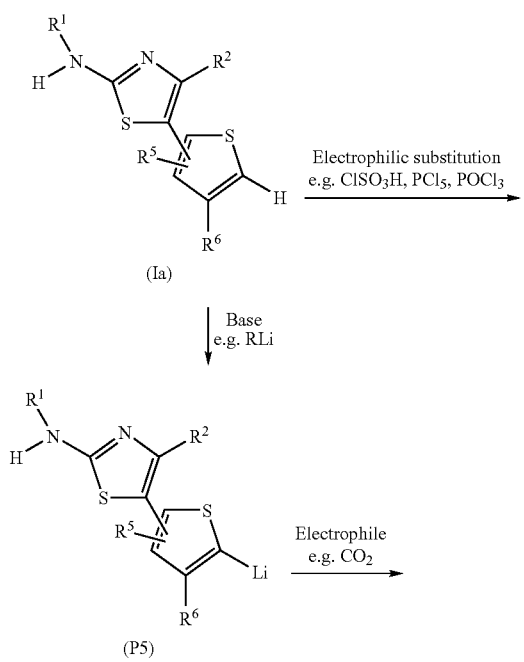

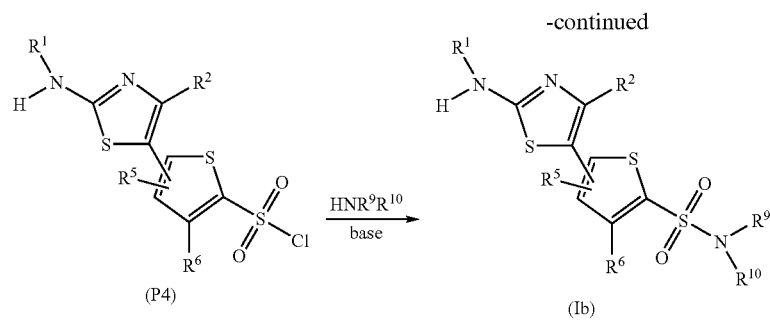

Formula (I) wherein
R⁴ = SO₂NR⁹R¹⁰

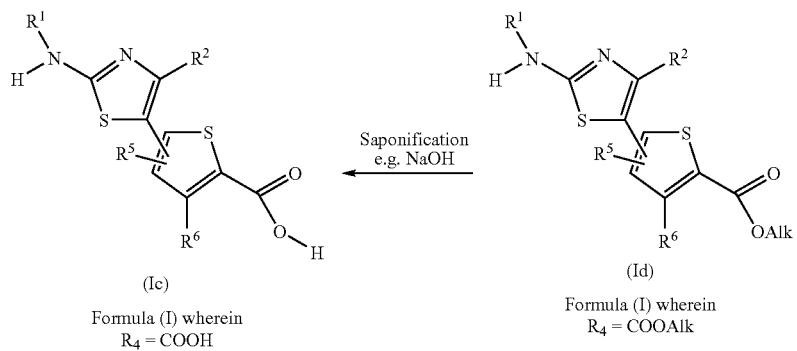

Compounds of Formula (Ic) may be also obtained by saponification of ester (Id) (Compounds of Formula (I) wherein $R^4=CO_2Alk$, where Alk may be any $C_1$-$C_6$ alkyl group, optionally substituted alkyl) (Scheme 3). Compounds (1d) may be prepared by cross-coupling reaction between (P1) and the suitable substituted thiophene (P2) or (P3).

Compounds of Formula (Ic) may be further transformed into the corresponding amide (Ie) (Compounds of Formula (I) wherein $R^4=CO_2NR^{11}R^{12}$ is an amino carbonyl as defined above and where $R^3$ may be T1 or T2) (Scheme 4, below). Amide (Ie) may be obtained by coupling of the corresponding carboxylic acid (Ic) with an amine $HNR^{11}R^{12}$, wherein $R^{11}$ and $R^{12}$ are selected from H, optionally substituted $C_1$-$C_6$-alkyl, optionally —$NR^{11}R^{12}$ may form a ring, and may be selected from substituted heterocycloalkyl, such as optionally substituted morpholine (e.g. morpholin-4-yl), optionally substituted piperidine (e.g. 4-hydroxypiperidin-1-yl, 3-hydroxypiperidin-1-yl), in the presence of an activating agent, such as DCC, EDC, HOBt, PyBOP, etc. Addition of a base, such as TEA or DIEA, may be needed, depending on the nature of the coupling agent. Solvents may be chosen between DCM, DMF, MeCN or any other solvents suitable for such transformation.

Scheme 4

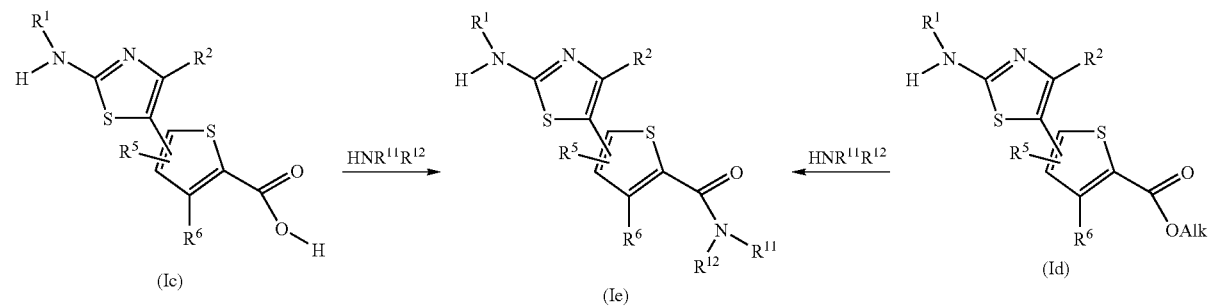

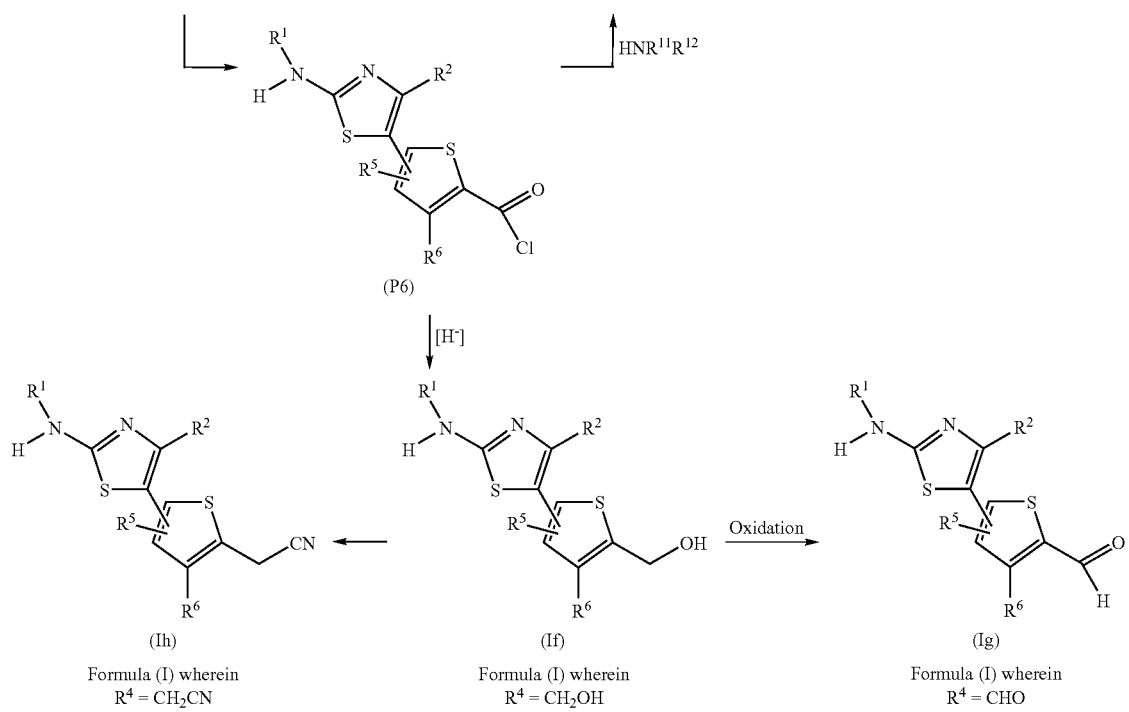

Carboxylic acid (Ic) may be first transformed into the corresponding acid chloride (P6), using a suitable reagent such as oxalyl chloride or thionyl chloride. Reaction of the resulting acid chloride with amine $HNR^{11}R^{12}$, as defined above, in the presence of a base, e.g. pyridine, DIEA, TEA, etc, may afford compounds of Formula (Ie) (Compounds of Formula (I) wherein $R^4=CO_2NR^{11}R^{12}$).

For amines with low boiling points, Compounds of Formula (Ie) may be obtained by heating ester (Id) in the amine $HNR^{11}R^{12}$ used as solvent under microwave action, wherein $R^{11}$ and $R^{12}$ have been defined above.

Alcohols of Formula (If) (Compounds of Formula (I) wherein $R^3$=T1 or T2 and $R^4$=$CH_2OH$) may be prepared by reduction of intermediate (P6), with addition of hydride such as lithium tri-tert-butoxyaluminohydride ($(tBuO)_3$ AlHLi). The corresponding aldehyde of Formula (Ig) (Compounds of Formula (I) wherein $R^3$=T1 or T2 and $R^4$=C(O)H) may be obtained by oxidation of alcohol (If), using conditions known by a person skilled in the art, such as Swern or Dess Martin oxidation.

Alcohols of Formula (If) (Compounds of Formula (I) wherein $R^3$=T1 or T2 and $R^4$=$CH_2OH$) may be further transformed into the corresponding thienyl acetonitrile (Ih) (Compound of Formula (I) wherein $R^3$=T1 or T3 and $R^4$=$CH_2CN$) in a two step process, transformation of the primary alcohol into a suitable leaving group such as a triflate or a chlorine, followed by a $SN^2$ reaction with NaCN as nucleophile.

Aldehyde (Ih) may be further transformed by reductive amination, affording compounds of Formula (Ii) (Compounds of Formula (I) wherein $R^3$=T1 or T2, $R^4$=$CH_2NR^{13}R^{14}$ and $R^{13}$ and $R^{14}$ are selected from H, optionally substituted $C_1$-$C_6$-alkyl, such as allyl.

Scheme 5

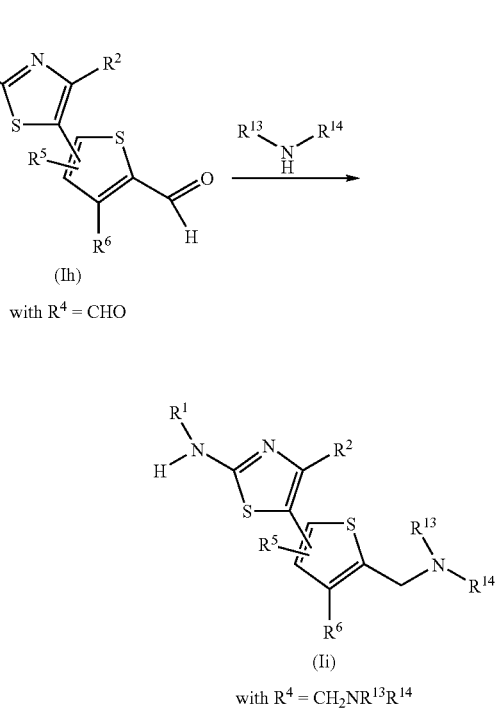

Reductive amination of aldehyde (Ih) may be performed in one or two steps. Amine $R^{13}R^{14}NH$, wherein $R^{13}$ and $R^{14}$ are selected from H, optionally substituted $C_1$-$C_6$-alkyl, such as allyl, and aldehyde (Ih) can be mixed in the presence of a reducing agent, such as NaHB(OAc) or NaBH$_3$CN, affording in one step compounds of Formula (Ii). The corresponding imine intermediate can be first isolated, before performing the reduction with a suitable reagent such as NaBH$_4$ or any other reagent known by a person skilled in the art.

Thiophene carbaldehyde (Ih) may be transformed into the corresponding thiophene carbonitrile (Ik) (Compound of Formula (I) wherein $R^3$=T1 or T2 and $R^4$=CN, as described above). Heating aldehyde (Ih), with 10 eq of hydroxylamine hydrochloride and 10 eq of pyridine, in a 1:1 EtOH/THF mixture, at 70° C., may afford carbaldehyde oxime (Ij) (Compound of Formula (I) wherein $R^4$CHNOH). It may be further transformed into the corresponding carbonitrile (Ik) by reacting with copper acetate in acetonitrile at 70° C. Carbonitrile (Ik) may be also prepared in a one-pot process, by performing the reaction of thiophene carbaldehyde (Ih) with hydroxylamine hydrochloride and mesyl chloride in DMF under microwave action.

Boronic ester (P2b) may be transformed into alternative boronic ester, using conditions known by a person skilled in the art.

Scheme 7

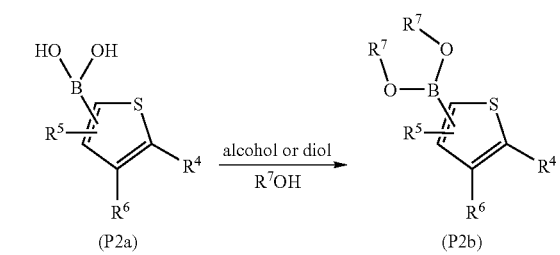

Pinacol boronic ester (P2c) may be prepared by a metal coupling reaction between the corresponding thiophene halide, (P4), where X=Br, I, etc, and bis(pinacolato)diboron (P5) or pinacol borane (P6) (Scheme 8 below). This reaction may be catalyzed by different palladium complexes may be used, such as Pd(PPh$_3$)$_4$, [1,1'-bis(diphenylphosphino)fer- Scheme 6

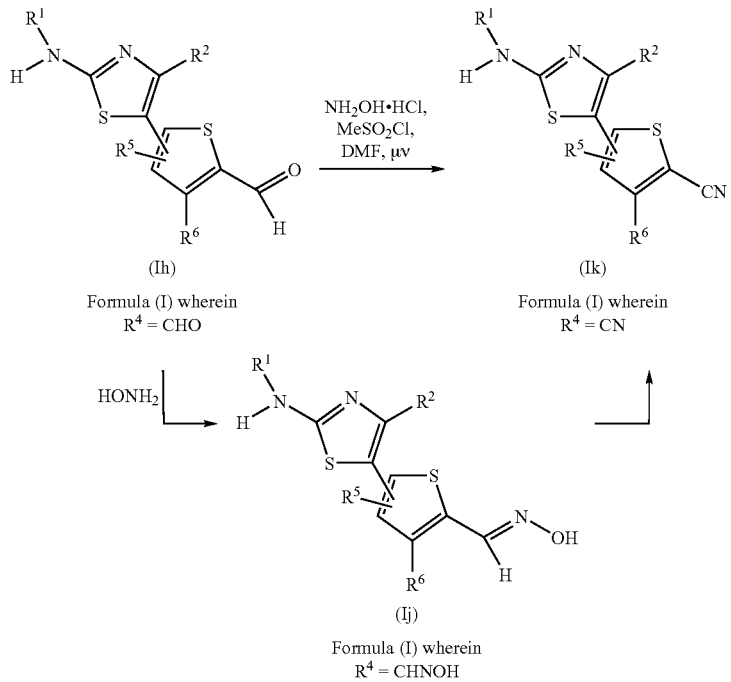

Compounds of Formula (Ia) to (Ik) may be obtained directly from a metal catalysed cross-coupling reaction, performing the reaction between (P1) and the suitable substituted thiophene (P2) or (P3).

Boronic acid or ester (P2) may be commercially available from various sources or synthesized, as it will be detailed below in the examples, using conditions known by a person skilled in the art. A boronic acid (P2a) may be transformed into the corresponding boronic ester (P2b), by heating (P2a) in the presence of an alcohol or a diol (Scheme 7 below).

rocene]palladium(II) chloride (Pd(dppf)Cl$_2$), PdCl$_2$(PPh$_3$)$_2$, Pd(OAc)$_2$, with the possible addition of phosphine ligands such as PPh$_3$.

Different organic or inorganic bases may be used, such as TEA, DIEA, KF, KOH, or any carbonate salts, such as K$_2$CO$_3$, Na$_2$CO$_3$, Cs$_2$CO$_3$. The solvent or solvents mixture may be selected between THF, Toluene, Dioxane, MeOH, MeCN, DMF, water, etc. The resulting reaction mixture may be heated, under inert atmosphere, at different temperatures, with the possible use of microwave action. All the different combinations described above may be used.

Scheme 8

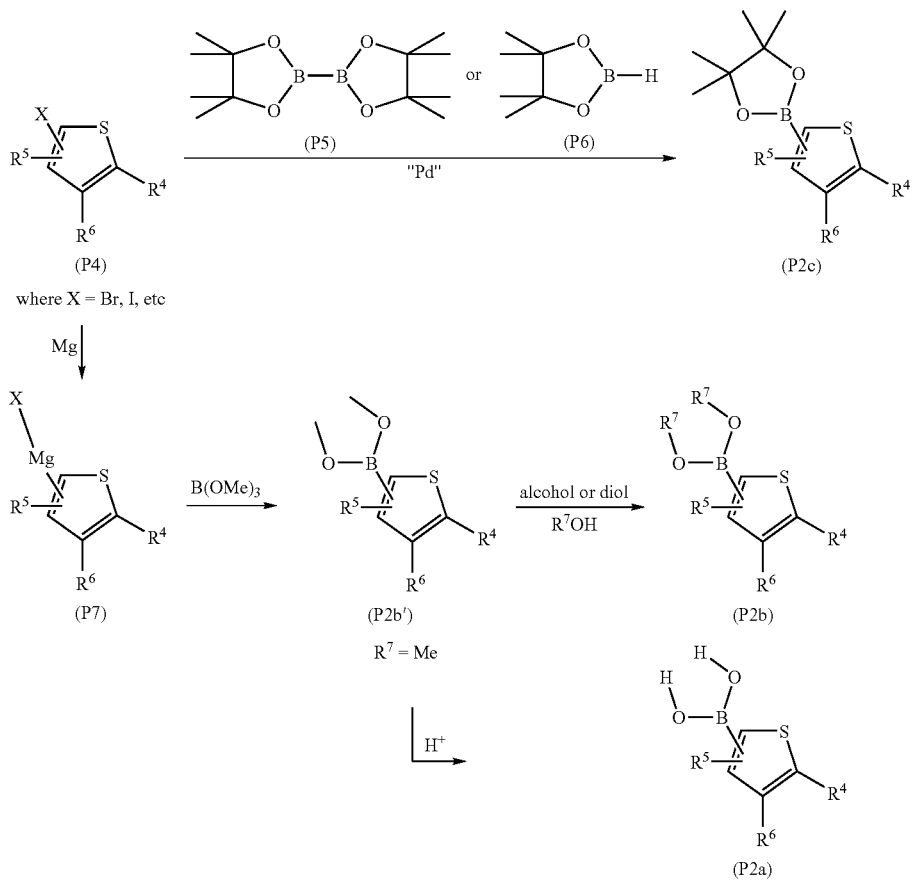

Thiophene halide (P4) may be first transformed into the corresponding thiophene Grignard reagent (P7), which may react with trialkylborate, e.g. B(OMe)₃, followed either by an acidic work-up to afford the corresponding boronic acid (P2a) or by a treatment with a suitable alcohol or diol R⁷OH to afford the corresponding boronic ester (P2b).

Direct 2-borylation may be obtained by iridium catalyzed reaction from 2-unsubstituted thiophene derivatives (P8) (Scheme 9 below). The iridium(I) complex generated from ½[Ir(OMe)(COD)]₂ and 4,4'-di-tert-butyl-2,2'-bipyridine catalyzed the direct borylation of thiophenes derivatives in stoichiometric amounts relative to bis(pinacolato)diboron, affording thiophene-2-boronic ester (P2c').

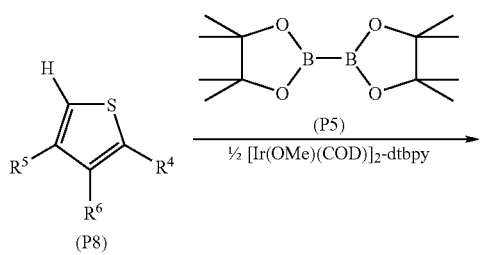

Scheme 9

-continued

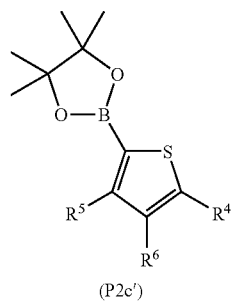

If the above set of conditions combination is not applicable to obtain boronic ester or acid (P2), suitable methods of preparation known by a person skilled in the art should be used.

Organotin reagents (P3) may be commercially available from various sources or synthesized, using conditions known by a person skilled in the art.

Compounds of formula (PI) with X=Br or I may be prepared by halogenation of the corresponding thiazole (P9) with reagents such as Br₂, I₂ or NBS, NIS (Scheme 10, below). Depending on the nature of R¹, protection of the secondary amine may be needed before the halogenation, with for example PG=acetyl or any other group which is easily removable.

Scheme 10

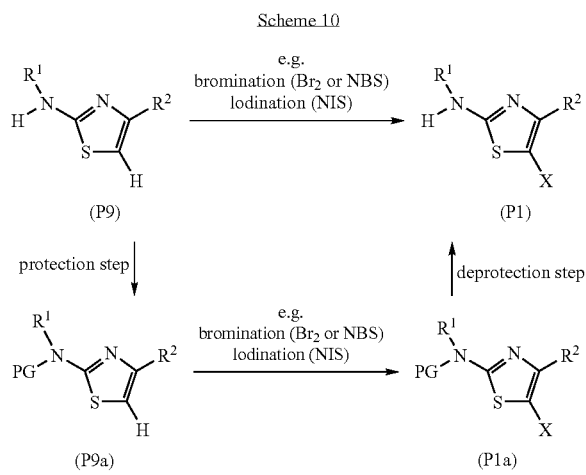

Thiazole (P9) may be commercially available from various sources or synthesized, using conditions known by a person skilled in the art, using both solution-phase and solid-phase chemistry protocols (Kodomari et al., 2002, above). For example, it may be obtained in two steps (Scheme 11 below), starting with α-halogenation of a ketone (P10), using for example $Br_2$ for a bromination or thionyl chloride for a chlorination, affording an intermediate (P11). "Hal" in intermediate (P11) can be also a tosyloxy group, which may be introduced with suitable reagents such as hydroxy(tosyloxy)iodobenzene. Intermediate (P11) may be then added to a solution of a substituted thiourea $R^1NHC(S)NH_2$ (P12) in a suitable solvent, preferably a polar solvent, e.g. EtOH, leading to intermediate (P9). The resulting intermediate (P11) may react with thiourea, affording thiazole (PI3) which may be further substituted with $R^1$, as defined above, using conditions known by a person skilled in the art.

Scheme 11

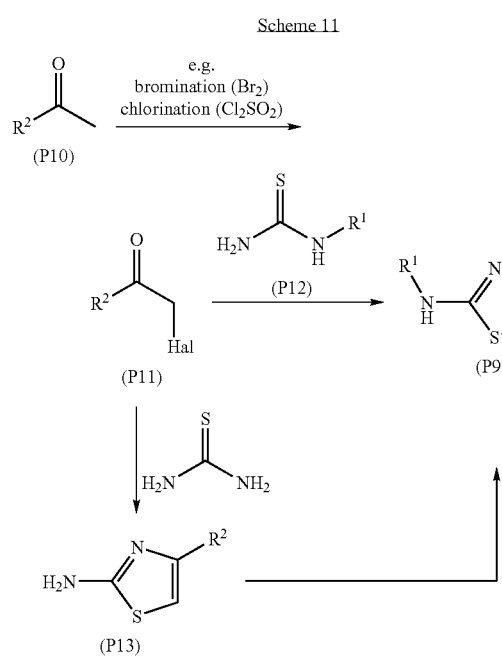

Thioureas (P12) used in synthetic Scheme 11 above are either commercially available from various sources or synthesized using conditions known by the person skilled in the art.

For example, thioureas (P12) can be obtained by coupling a salt of an amine $R^1NH_2$, preferably HCl salt, with potassium thiocyanate used in equimolarity in THF under reflux as shown on Scheme 4 below, Pathway A.

Scheme 12

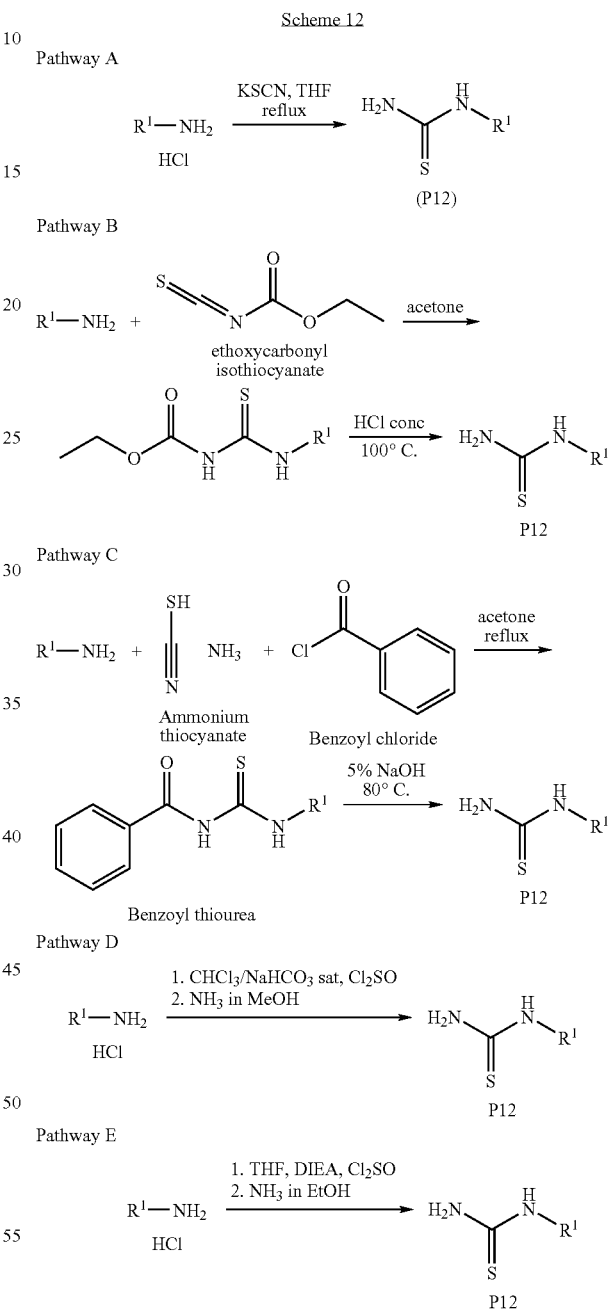

The amine $R^1NH_2$ can be first activated with ethoxycarbonyl isothiocyanate affording an ethoxycarbonyl thiourea intermediate, as presented above on Scheme 12, Pathway B. Upon deprotection under acidic conditions, e.g. concentrated HCl, the desired thiourea (P12) is released. The amine $R^1NH_2$ can be also activated with benzoyl isothiocyanate, which is obtained by addition of benzoyl chloride to ammonium thiocyanate, giving a benzoyl thiourea intermediate, as shown above on Scheme 12, Pathway C. Upon deprotection under basic conditions, e.g. NaOH, the desired thiourea (P12) is released. Alternatively, the amine R¹NH₂ can react with thiophosgene, followed by the addition of ammonia, as presented above on Scheme 12, Pathway D. If the above set of synthetic methods are not applicable to obtain N-substituted thiourea (P12), suitable methods of preparation known by a person skilled in the art should be used.

Methods of Preparing Intermediates of Compounds of Formula (I).

According to a further general process, compounds of Formula (I) can be converted to alternative compounds of Formula (I), employing suitable interconversion techniques well known by a person skilled in the art.

If the above set of general synthetic methods is not applicable to obtain compounds according to Formula (I) and/or necessary intermediates for the synthesis of compounds of Formula (I), suitable methods of preparation known by a person skilled in the art should be used. In general, the synthesis pathways for any individual compound of Formula (I) will depend on the specific substituents of each molecule and upon the ready availability of intermediates necessary; again such factors being appreciated by those of ordinary skill in the art. For all the protection and deprotection methods, see Philip J. Kocienski, in "*Protecting Groups*", Georg Thieme Verlag Stuttgart, N.Y., 1994 and, Theodora W. Greene and Peter G. M. Wuts in "*Protective Groups in Organic Synthesis*", Wiley Interscience, 3rd Edition 1999.

Compounds of this invention can be isolated in association with solvent molecules by crystallization from evaporation of an appropriate solvent. The pharmaceutically acceptable acid addition salts of the compounds of Formula (I), which contain a basic center, may be prepared in a conventional manner. For example, a solution of the free base may be treated with a suitable acid, either neat or in a suitable solution, and the resulting salt isolated either by filtration or by evaporation under vacuum of the reaction solvent. Pharmaceutically acceptable base addition salts may be obtained in an analogous manner by treating a solution of compound of Formula (I) with a suitable base. Both types of salts may be formed or interconverted using ion-exchange resin techniques.

In the following the present invention shall be illustrated by means of some examples, which are not construed to be viewed as limiting the scope of the invention.

EXAMPLES

The following starting materials commercially available were used:

PyBOP (Novabiochem), 2-(tributylstannyl)thiophene (Aldrich), 5-(dihydroxyboryl)-2-thiophenecarboxylic acid (Acros), 3-(4,4,5,5-tetramethyl-1,3,2-dioxaborolan-2-yl) thiophene (Boron-Mol), 5-formyl-2-thiopheneboronic acid (Aldrich), 2-acetamido-4-methylthiazole (Aldrich), pinacol (Aldrich), (trimethylsilyl)diazomethane 2N solution (Aldrich), Pd(dppf)Cl₂ (Avocado), cesium carbonate (Fluka), potassium fluoride (Fluka), copper acetate (Fluka), allylamine (Fluka), morpholine (Fluka), ethanolamine (Fluka), 4-hydroxypiperidine (Aldrich), 3-hydroxypiperidine (Aldrich), ammonia in MeOH 2N solution (Aldrich), 1,4-Dioxa-8-azaspiro[4.5]decane (Aldrich), chlorosulfonic acid (Fluka), phosphorus pentachloride (Aldrich), phosphorus oxide chloride (Aldrich), hydroxylamine hydrochloride (Fluka).

The HPLC, NMR and MS data provided in the examples described below are obtained as followed: HPLC: column Waters Symmetry C8 50×4.6 mm, Conditions: MeCN/H₂O, 5 to 100% (8 min), max plot 230-400 nm; Mass spectra: PE-SCIEX API 150 EX (APCI and ESI), LC/MS spectra: Waters ZMD (ES); ¹H-NMR: Bruker DPX-300 MHz.

The preparative HPLC purifications are performed with HPLC Waters Prep LC 4000 System equipped with columns Prep Nova-Pak®HR C186 μm 60Å, 40×30mm (up to 100 mg) or with XTerra® Prep MS C8, 10 μm, 50×300mm (up to 1g). All the purifications are performed with a gradient of MeCN/H₂O 0.09% TFA. The semi-preparative reverse-phase HPLC are performed with the Biotage Parallex Flex System equipped with columns Supelcosil™ ABZ+Plus (25 cm× 21.2 mm, 12 μm); UV detection at 254 nm and 220 nm; flow 20 ml/min (up to 50 mg). TLC Analysis is performed on Merck Precoated 60 F₂₅₄ plates. Purifications by flash chromatography are performed on SiO₂ support, using cyclohexane/EtOAc or DCM/MeOH mixtures as eluents.

The microwave chemistry is performed on a single mode microwave reactor Emrys™ Optimiser from Personal Chemistry.

Intermediate 1: Preparation of N-(5-iodo-4-methyl-1, 3-thiazol-2-yl)acetamide (Intermediate (P1) wherein R¹ is C(O)CH₃, R² is CH₃ and X is I)

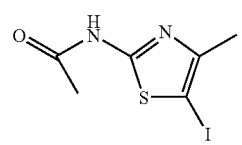

Intermediate 1

To a solution of 2-Acetamido-4-methylthiazole (5 g; 32.01 mmol; 1 eq.) in MeCN (100 ml) is added N-iodosuccinimide (8.642 g; 38.41 mmol; 1.2 eq.). The resulting homogeneous solution is stirred at rt. After 5 min, a precipitate is formed. It is filtrated and washed with cold MeCN. A first batch of Intermediate 1 is isolated as white-off solid (5.072 g; 57%). The mother liquors are evaporated and dissolved in EtOAc. They are washed with two fraction of Na₂S₂O₃ 1N solution and dried over MgSO₄. After filtration and evaporation of the solvents, the resulting solid is suspended in MeCN, filtrated and dried under vacuo, affording a second batch of Intermediate 1 as white-off solid (1.813 g; 20%). The overall yield of this reaction is 77%. ¹H NMR (DMSO-d₆, 300 MHz) δ 1.88 (s, 3H), 2.02 (s, 3H), 12.02 (s, 1H). M⁻(ESI): 281.02; M⁺(ESI): 283.09. HPLC, Rt: 2.55 min (purity: 100%).

Intermediate 2: Preparation of Methyl 5-(4,4,5,5-tetramethyl-1,3,2-dioxaborolan-2-yl)thiophene-2-carboxylate (Intermediate P2c wherein R⁵=R²=H and R⁴=C(O)CH₃)

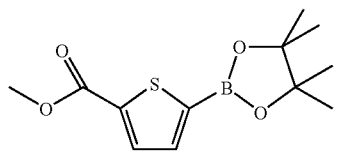

Intermediate 2

Step 1: 5-(4,4,5,5-tetramethyl-1,3,2-dioxaborolan-2-yl)thiophene-2-carboxylic acid 5-(Dihydroxyboryl)-2-thiophenecarboxylic acid (1 g; 5.82 mmol; 1 eq.) is dissolved in a mixture of Et₂O (100 ml) and MeOH (5 ml). Pinacol (687.2 mg; 5.82 mmol; 1 eq.) is added. The reaction mixture is stirred at rt for 24 hours. To complete the reaction, some pinacol is added (200 mg; 1.7 mmol; 0.3 eq.) and the mixture is stirred for 12 additional hours. Water (50 ml) is added and the two phases are separated. Aqueous phase is extracted with ether (50 ml). Combined organic phases is dried over MgSO₄, filtrated and evaporated, affording 5-(4,4,5,5-tetramethyl-1,3,2-dioxaborolan-2-yl) thiophene-2-carboxylic acid as white-off solid (1.33 g; 90%). ¹H NMR (DMSO-d₆, 300 MHz) δ 1.13 (s, 12H), 7.37 (d, J=3.8 Hz, 1H), 7.58 (d, J=3.8 Hz, 1H), 13.12 (s, 1H). M⁻(ESI): 253. HPLC, Rt: 0.98 min (purity: 100%).

Step 2: methyl 5-(4,4,5,5-tetramethyl-1,3,2-dioxaborolan-2-yl)thiophene-2-carboxylate 5-(4,4,5,5-Tetramethyl-1,3,2-dioxaborolan-2-yl) thiophene-2-carboxylic acid (1.33 g; 5.23 mmol; 1 eq.) is dissolved in MeOH (60 ml) and toluene (14 ml). A (trimethylsilyl)diazomethane solution (7.85 ml; 2 M; 15.70 mmol; 3 eq.) is added dropwise. The resulting mixture is stirred 5 hours at rt. To complete the reaction, (trimethylsilyl)diazomethane solution (7.85 ml; 2 M; 15.70 mmol; 3 eq.) is added. After 3 hours, the conversion is complete. Solvents are evaporated and the resulting solid is recrystallized in MeOH, affording Intermediate 2 as white-off solid (1087 mg; 77.5%). ¹H NMR (DMSO-d₆, 300 MHz) δ 1.29 (s, 12H), 3.83 (s, 3H), 7.56 (d, J=3.8 Hz, 1H), 7.82 (d, J=3.8 Hz, 1H). M⁺(ESI): 269.23. HPLC, Rt: 1.83 min (purity: 99.67%).

Example 1

N-[5-(5-formyl-2-thienyl)-4-methyl-1,3-thiazol-2-yl]acetamide (1)

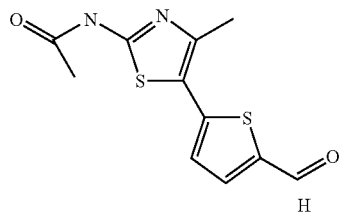

N-(5-iodo-4-methyl-1,3-thiazol-2-yl)acetamide, Intermediate 1 (3.300 g; 11.70 mmol; 1 eq.), 5-formyl-2-thiopheneboronic acid (2.737 g; 17.55 mmol; 1.50 eq.), triethylamine (4.86 ml; 35.09 mmol; 3 eq.) are dissolved in DMF (70 ml). The mixture is degassed with argon, Pd(dppf)Cl₂ (428 mg; 0.58 mmol; 0.05 eq.) is added and the mixture is heated at 95° C. for 2 h. The solvents are evaporated and the crude mixture is suspended in THF. It is filtrated, affording Compound (1) as a brown solid (864 mg; 28%). ¹H NMR (DMSO-d₆, 300 MHz) δ 2.23 (s, 3H), 2.56 (s, 3H), 7.45 (d, J=3.8 Hz, 1H), 8.08 (d, J=3.8 Hz, 1H), 9.96 (s, 1H), 12.44 (s, 1H). M⁻(ESI): 265.10; M⁺(ESI): 267.14. HPLC, Rt: 2.77 min (purity: 93.3%).

Example 2

N-(5-{5-[(allylamino)methyl]-2-thienyl}-4-methyl-1,3-thiazol-2-yl)acetamide (2)

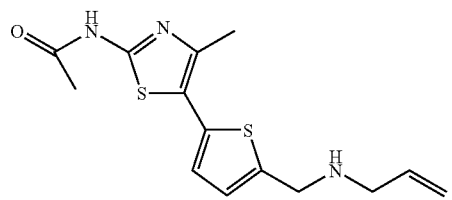

Step 1: N-(5-{5-[(E)-(allylimino)methyl]-2-thienyl}-4-methyl-1,3-thiazol-2-yl)acetamide Anhydrous magnesium sulfate (94 mg; 0.78 mmol; 4.15 eq.) and N-[5-(5-formyl-2-thienyl)-4-methyl-1,3-thiazol-2-yl]acetamide, Compound (1), (50 mg; 0.19 mmol; 1 eq.), are added to a solution of allylamine (17 µl; 0.23 mmol; 1.20 eq.) and acetic acid (16 µl; 0.28 mmol; 1.50 eq.) in dry THF (5 ml). The reaction is stirred at rt overnight. The mixture is filtered and rinsed with anhydrous THF and DCM, affording N-(5-{5-[(E)-(allylimino)methyl]-2-thienyl}-4-methyl-1,3-thiazol-2-yl)acetamide which is used in the next step without further purification (57.3 mg, quantitative).

Step 2: N-(5-{5-[(allylamino)methyl]-2-thienyl}-4-methyl-1,3-thiazol-2-yl)acetamide (2)

N-(5-{5-[(E)-(allylimino)methyl]-2-thienyl}-4-methyl-1,3-thiazol-2-yl)acetamide, obtained in Step 1 as described above (57.3 mg; 0.19 mmol; 1 eq.), is dissolved in 4 ml of MeOH. NaBH₄ (7.1 mg; 0.19 mmol; 1 eq.) is added. After one night, a second fraction of NaBH₄ (7.1 mg; 0.19 mmol; 1 eq.) is added, in order to complete the reduction. Water is added to quench the reaction (2 ml) and the solvents are concentrated. Aqueous phase is acidified with HCl 1N and is washed with AcOEt. It is then basified with NaHCO₃, and the desired product is extracted with AcOEt. The combined organic layers are dried over magnesium sulfate, filtered and concentrated, affording Compound (2) as an orange solid (24.1 mg; 42%). ¹H NMR (DMSO-d₆, 300 MHz) δ 2.12 (s, 3H), 2.37 (s, 3H), 3.16 (m, 2H), 3.83 (s, 2H), 5.11 (m, 2H), 5.83 (m, 1H), 6.92 (m, 3H), 12.13 (m, 1H). M⁻(ESI): 306.19; M⁺(ESI): 308.24. HPLC, Rt: 1.82 min (purity: 80.6%).

Example 3

N-[5-[5-(hydroxymethyl)-2-thienyl]-4-methyl-1,3-thiazol-2-yl]acetamide (3)

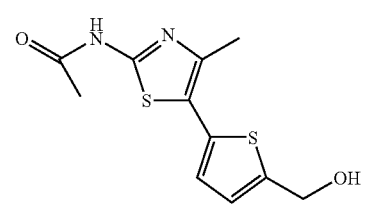

N-[5-(5-formyl-2-thienyl)-4-methyl-1,3-thiazol-2-yl]acetamide, Compound (1) obtained as described above (25 mg; 0.09 mmol; 1 eq.), is dissolved in MeOH (2 ml) and sodium borohydride (3.6 mg; 0.09 mmol; 1 eq.) is added. After one night, a second fraction of NaBH₄ (7.1 mg; 0.19 mmol; 1 eq.) is added, in order to complete the reduction. Water is added to quench the reaction (1 ml) and the solvents are concentrated. Aqueous phase is neutralized with HCl 1N and the desired product is extracted with AcOEt. The combined organic layers are dried over magnesium sulfate, filtered and concentrated, affording Compound (3) as an orange solid (19.4 mg; 77%). ¹H NMR (DMSO-d⁶) δ 2.12 (s, 3H), 2.38 (s, 3H), 4.61 (d, J=6 Hz, 2H), 5.51 (t, J=6 Hz, 1H), 6.93 (d, J=3.8 Hz, 1H), 6.99 (d, J=3.8 Hz, 1H), 12.15 (br s, 1H). M⁻(ESI): 267.15; M⁺(ESI): 269.20. HPLC, Rt: 2.26 min (purity: 90.1%).

Example 4

5-[2-(acetylamino)-4-methyl-1,3-thiazol-5-yl]thiophene-2-carboxylic acid (4)

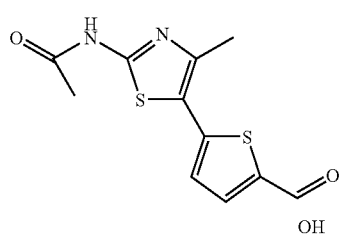

(4)

N-(5-iodo-4-methyl-1,3-thiazol-2-yl)acetamide, Intermediate 1 (550 mg; 1.95 mmol; 1 eq.), 5-(dihydroxyboryl)-2-thiophenecarboxylic acid (335.3 mg; 1.95 mmol; 1 eq.), cesium carbonate (1397.5 mg; 4.29 mmol; 2.20 eq.), Pd(dppf)Cl₂ (57.1 mg; 0.08 mmol; 0.04 eq.) are put in a microwave reactor, followed by DMF (8 ml) and water (4 ml). The reaction mixture is flushed with argon and is heated under microwave action for 10 min at 150° C. It is filtered through a paper filter, diluted with HCl 1N solution (10 ml) and the desired product is extracted with EtOAc. Combined organic layer is dried over MgSO₄, filtered and evaporated. The crude product is purified by preparative HPLC, affording Compound (4) as white-off solid (125 mg; 22.7%). ¹H NMR (DMSO-d⁶) δ 2.14 (s, 3H), 2.44 (s, 3H), 7.21 (d, J=3.8 Hz, 1H), 7.67 (d, J=3.8 Hz, 1H), 12.30 (s, 1H), 13.15 (br s, 1H). M⁻(ESI): 281; M⁺(ESI): 283. HPLC, Rt: 2.54 min (purity: 99.9%).

Example 5

N-{4-methyl-5-[5-morpholin-4-ylcarbonyl)-2-thienyl]-1,3-thiazol-2-yl}acetamide (5)

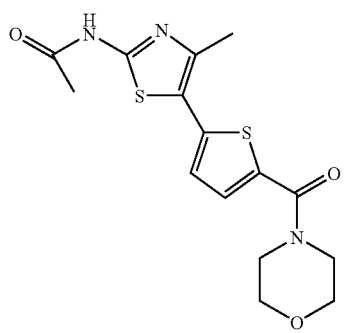

(5)

5-[2-(Acetylamino)-4-methyl-1,3-thiazol-5-yl]thiophene-2-carboxylic acid, Compound (4) obtained as described above (24 mg; 0.09 mmol; 1 eq.), is dissolved in THF (4 ml). PyBOP (66.4 mg; 0.13 mmol; 1.50 eq.), DIEA (0.03 ml; 0.17 mmol; 2 eq.) and morpholine (0.02 ml; 0.26 mmol; 3 eq.) are added successively. The reaction mixture is stirred at room temperature overnight. The solvents are evaporated and CH₃CN is added. The resulting precipitate is filtered, affording Compound (5) as yellow solid (5 mg; 33%). ¹H NMR (DMSO-d⁶) δ 2.14 (s, 3H), 2.43 (s, 3H), 3.55-3.78 (m, 8H), 7.15 (d, J=3.8 Hz, 1H), 7.41 (d, J=3.8 Hz, 1H), 12.15 (br s, 1H). M⁻(ESI): 350.06; M⁺(ESI): 352.06. HPLC, Rt: 2.61 min (purity: 97.2%).

Example 6

N-[4-methyl-5-(2-thienyl)-1,3-thiazol-2-yl]acetamide (6)

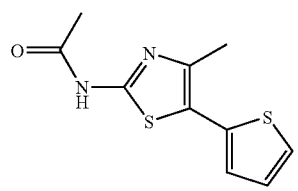

(6)

N-(5-iodo-4-methyl-1,3-thiazol-2-yl)acetamide, Intermediate 1 (2 g; 7.09 mmol; 1 eq.) and Pd(dppf)Cl₂ (0.52 g; 0.71 mmol; 0.10 eq.) are dissolved in DMF (35 ml). 2-(Tributylstannyl)thiophene (2.68 ml; 8.44 mmol; 1.19 eq.) is added. The reaction mixture is flushed with argon and heated at 100° C. for 1 h30. Solvents are evaporated and the crude mixture is dissolved in EtOAc (100 ml), washed with water (3×100 ml). The aqueous phase are combined and extracted with EtOAc (2×50 ml). Combined organic phases is washed with brine and dried over MgSO₄. After evaporation of the solvents, the crude product is purified by preparative HPLC, affording Compound (6) as white-off powder (1.24 g; 73.5%). ¹H NMR (DMSO-d⁶) δ 2.16 (s, 3H), 2.42 (s, 3H), 7.15 (dd, J=3.8, 5.3 Hz, 1H), 7.20 (dd, J=1.1, 3.8 Hz, 1H), 7.60 (dd, J=1.1, 5.3 Hz, 1H), 12.19 (s, 1H). M⁻(ESI): 237.01; M⁺(ESI): 239.01. HPLC, Rt: 3.01 min (purity: 98.7%).

Example 7

N-(5-{5-[(4-hydroxypiperidin-1-yl)carbonyl]-2-thienyl}-4-methyl-1,3-thiazol-2-yl)acetamide (7)

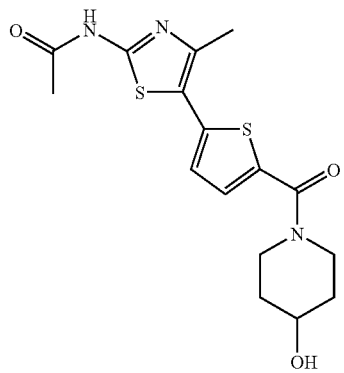

(7)

5-[2-(Acetylamino)-4-methyl-1,3-thiazol-5-yl]thiophene-2-carboxylic acid, Compound (4) (50 mg; 0.18 mmol; 1 eq.), is dissolved in THF (8 ml). PyBOP (138.2 mg; 0.27 mmol; 1.50 eq.), 4-hydroxypiperidine (53.7 mg; 0.53 mmol; 3 eq.) and DIEA (0.06 ml; 0.35 mmol; 2 eq.) are added successively. The reaction mixture is stirred at room temperature for 2 hours. The solvents are evaporated and the crude product is suspended in MeCN, filtered and washed several times with MeCN, affording Compound (7) as brown solid (15.2 mg; 23%). $^1$H NMR (DMSO-d$^6$) δ 1.30-1.45 (m, 2H), 1.72-1.85 (m, 2H), 2.14 (s, 3H), 2.42 (s, 3H), 3.25-3.38 (m, 2H), 3.75 (m, 1H), 3.85-4.02 (m, 2H), 4.80 (d, J=6 Hz, 1H), 7.13 (d, J=6 Hz, 1H), 7.36 (d, J=6 Hz, 1H), 12.18 (br s, 1H). M$^-$(ESI): 364.12; M$^+$(ESI): 366.10. HPLC, Rt: 2.35 min (purity: 97.9%).

Example 8

N-(5-{5-[(3-hydroxypiperidin-1-yl)carbonyl]-2-thienyl}-4-methyl-1,3-thiazol-2-yl)acetamide (8)

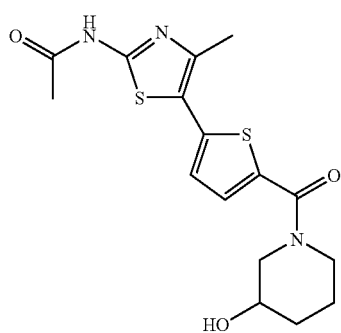
(8)

5-[2-(Acetylamino)-4-methyl-1,3-thiazol-5-yl]thiophene-2-carboxylic acid, Compound (4) obtained as described above (40 mg; 0.14 mmol; 1 eq.), is dissolved in THF (8 ml). PyBOP (110.6 mg; 0.21 mmol; 1.50 eq.), 3-hydroxypiperidine (43.0 mg; 0.43 mmol; 3 eq.) and DIEA (0.05 ml; 0.28 mmol; 2 eq.) are added successively. The reaction mixture is stirred at room temperature for 2 hours. The solvents are evaporated and the crude product is suspended in MeCN, filtered and washed several times with MeCN, affording Compound (8) as white-off (35.6 mg; 65%). $^1$H NMR (DMSO-d$^6$) δ 1.38-1.52 (m, 2H), 1.68-1.88 (m, 3H), 2.14 (s, 3H), 2.42 (s, 3H), 2.95-3.05 (m, 1H), 3.50-3.62 (m, 1H), 3.68-3.80 (m, 1H), 3.864 (m, 1H), 4.96 (d, J=4 Hz, 1H), 7.13 (d, J=3.8 Hz, 1H), 7.38 (d, J=3.8 Hz, 1H), 12.18 (br s, 1H). M$^-$(ESI): 364.12; M$^+$(ESI): 366.11. HPLC, Rt: 2.48 min (purity: 94.5%).

Example 9

N-(5-{5-[(3-hydroxypiperidin-1-yl)sulfonyl]-2-thienyl}-4-methyl-1,3-thiazol-2-yl)acetamide (9)

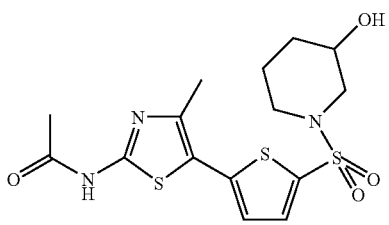
(9)

Step 1: 5-[2-(acetylamino)-4-methyl-1,3-thiazol-5-yl]thiophene-2-sulfonyl chloride N[4-methyl-5-(2-thienyl)-1,3-thiazol-2-yl]acetamide, Compound (6) (500 mg; 2.10 mmol; 1eq.) is dissolved in DCM (30 ml). The reaction mixture is cooled down to 0° C. and chlorosulfonic acid (0.70 ml; 10.49 mmol; 5 eq.) dissolved in DCM (30 ml) is added dropwise over 15 min. The solution becomes pink. It is stirred 15 minutes at 0° C. Phosphorus pentachloride (873.7 mg; 4.20 mmol; 2 eq.) and phosphorus oxide chloride (0.78 ml; 8.39 mmol; 4 eq.) are added successively. The reaction mixture is stirred for 2 additional hours at room temperature. It is poured on ice and the desired product is extracted with 2 portions of EtOAc, dried over MgSO$_4$, and evaporated, affording 5-[2-(acetylamino)-4-meththyl-1,3-thiazol-5-yl]thiophene-2-sulfonyl chloride as yellow solid (650 mg; 92%). M$^-$(ESI): 335.08; M$^+$(ESI): 337.08.

Step 2: N-(5-[(5-[(3-hydroxypiperidin-1-yl)sulfonyl]-2-thienyl]-4-methyl-1,3-thiazol-2-yl)acetamide (9)

5-[2-(acetylamino)-4-methyl-1,3-thiazol-5-yl]thiophene-2-sulfonyl chloride, prepared in Step 1 (110 mg; 0.33 mmol; 1 eq.), is dissolved in DCM (10 ml). 3-Hydroxypiperidine (66.1 mg; 0.65 mmol; 2 eq.) and DIEA (0.17 ml; 0.98 mmol; 3 eq.) are added. After one hour, the solvents are evaporated. The crude product is dissolved in DCM and washed with NH$_4$Cl saturated solution, water and dried over MgSO$_4$. After evaporation of the solvents, Compound (9) is obtained as white-off solid (35 mg; 26.5%). $^1$H NMR (DMSO-d$^6$) δ 0.88-1.04 (m, 1H), 1.17-1.35 (m, 1H), 1.46-1.63 (m, 2H), 1.94 (s, 3H), 2.11 (m, 1H), 2.24 (s, 3H), 2.27-2.38 (m, 2H), 3.20 (m, 1H), 3.37 (m, 1H), 4.80 (d, J=4.5 Hz, 2H), 7.08 (d, J=3.8 Hz, 1H), 7.37 (d, J=3.8 Hz, 1H), 12 (br s, 1H). M$^-$(ESI): 400.20; M$^+$(ESI): 402.10. HPLC, Rt: 2.90 min (purity: 99.2%).

Example 10

N-(5-[5-[(4-hydroxypiperidin-1-yl)sulfonyl]-2-thienyl]-4-methyl-1,3-thiazol-2-yl)acetamide (10)

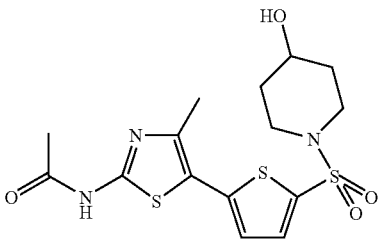
(10)

5-[2-(acetylamino)-4-methyl-1,3-thiazol-5-yl]thiophene-2-sulfonyl chloride, prepared as in Step 1 of Example 9 (110 mg; 0.33 mmol; 1 eq.), is dissolved in DCM (10 ml). 4-Hydroxypiperidine (66.1 mg; 0.65 mmol; 2 eq.) and DIEA (0.17 ml; 0.98 mmol; 3 eq.) are added. After one hour, the solvents are evaporated. The crude product is dissolved in DCM and washed with NH$_4$Cl saturated solution, water and dried over MgSO$_4$. After evaporation of the solvents, Compound (10) is obtained as white-off solid (33 mg; 23%). $^1$H NMR (DMSO-d$^6$) δ 1.40-1.60 (m, 2H), 1.72-1.85 (m, 2H), 2.14 (s, 3H), 2.42 (s, 3H), 2.80-2.92 (m, 2H), 3.15-3.30 (m, 2H), 3.59 (m, 1H), 4.71 (d, J=3 Hz, 1H), 7.30 (d, J=4.5 Hz, 1H), 7.58 (d, J=4.5 Hz, 1H), 12.18 (br s, 1H). M⁻(ESI): 400.20; M⁺(ESI): 402.10. HPLC, Rt: 2.86 min (purity: 100%).

Example 11

N-[5-(5-{[(2-hydroxyethyl)amino]sulfonyl}-2-thienyl)-4-methyl-1,3-thiazol-2-yl]acetamide (11)

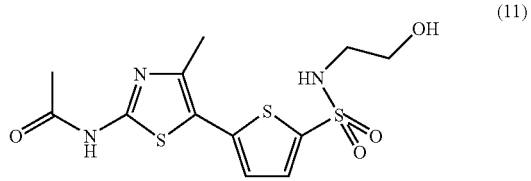

5-[2-(acetylamino)-4-methyl-1,3-thiazol-5-yl]thiophene-2-sulfonyl chloride, prepared as in Step 1 of Example 9 (110 mg; 0.33 mmol; 1 eq.), is dissolved in DCM (10 ml). Ethanolamine (39.9 mg; 0.65 mmol; 2 eq.) and DIEA (0.17 ml; 0.98 mmol; 3 eq.) are added. After one hour, the solvents are evaporated. The crude product is dissolved in DCM and washed with NH₄Cl saturated solution, water and dried over MgSO₄. After evaporation of the solvents, Compound (11) is obtained as white-off solid (36.5 mg; 30%). ¹H NMR (DMSO-d⁶) δ 2.15 (s, 3H), 2.43 (s, 3H), 2.91 (m, 2H), 3.41 (m, 2H), 4.72 (t, J=6 Hz, 1H), 7.21 (d, J=4.5 Hz, 1H), 7.54 (d, J=4.5 Hz, 1H), 7.88 (br s, 1H), 12.25 (br s, 1H). M⁻(ESI): 360.11; M⁺(ESI): 362.06. HPLC, Rt: 2.36 min (purity: 97.5%).

Example 12

N-(5-[5-{(allylamino)sulfonyl]-2-thienyl}-4-methyl-1,3-thiazol-2-yl) acetamide (12)

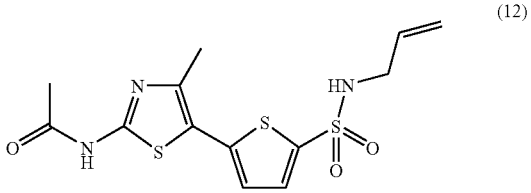

5-[2-(acetylamino)-4-methyl-1,3-thiazol-5-yl]thiophene-2-sulfonyl chloride, prepared as in Step 1 of Example 9 (110 mg; 0.33 mmol; 1 eq.), is dissolved in DCM (10 ml). Allylamine (0.034 ml; 0.46 mmol; 1.40 eq.) and DIEA (0.17 ml; 0.98 mmol; 3 eq.) are added. After one hour, the solvents are evaporated. The crude product is purified by preparative HPLC, affording Compound (12) is obtained as white-off solid (75 mg; 50%). ¹H NMR (DMSO-d⁶) δ 2.22 (s, 3H), 2.51 (s, 3H), 3.61 (m, 2H), 5.14 (m, 1H), 5.26 (m, 1H), 5.80 (m, 1H), 7.28 (d, J=3.8 Hz, 1H), 7.62 (d, J=3.8 Hz, 1H), 8.17 (t, J=6 Hz, 1H), 12.39 (s, 1H). M⁻(ESI): 356.12; M⁺(ESI): 358.12. HPLC, Rt: 3.06 min (purity: 100%).

Example 13

N-{4-methyl-5-[5-(morpholin-4-ylsulfonyl)-2-thienyl]-1,3-thiazol-2-yl}acetamide (13)

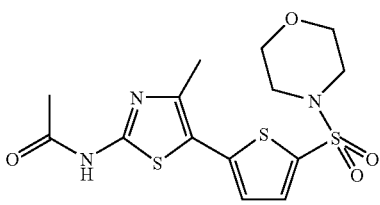

5-[2-(acetylamino)-4-methyl-1,3-thiazol-5-yl]thiophene-2-sulfonyl chloride, prepared as in Step 1 of example 9 (110 mg; 0.33 mmol; 1 eq.), is dissolved in DCM (10 ml). Morpholine (0.04 ml; 0.46 mmol; 1.40 eq.) and DIEA (0.17 ml; 0.98 mmol; 3 eq.) are added. After one hour, the solvents are evaporated. The crude product is purified by preparative HPLC, affording Compound (13) is obtained as white-off solid (15 mg; 19%). ¹H NMR (DMSO-d⁶) δ 2.15 (s, 3H), 2.46 (s, 3H), 2.96 (m, 4H), 3.67 (m, 4H), 7.33 (d, J=3.8 Hz, 1H), 7.61 (d, J=3.8 Hz, 1H), 12.35 (s, 1H). M⁻(ESI): 386.17; M⁺(ESI): 388.46. HPLC, Rt: 3.21 min (purity: 99.7%).

Example 14

N-(5-{5-[(hydroxyimino)methyl]-2-thienyl}-4-methyl-1,3-thiazol-2-yl)acetamide (14)

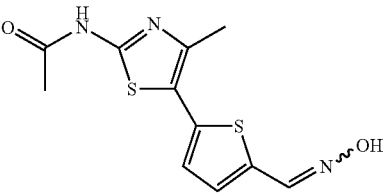

N-[2-(5-Formyl-thiophen-2-yl)-4-methyl-thiazol-5-yl]-acetamide, Compound (1) (104 mg; 0.39 mmol; 1 eq.), is dissolved in a THF/Ethanol 1:1 mixture (10 ml) at room temperature. Hydroxylamine hydrochloride (275 mg; 3.9 mmol; 10 eq.) and pyridine (310 μl; 3.9 mmol; 10.0 eq.) are added and reaction mixture is heated at 70° C. for 30 minutes. Reaction mixture is cooled down to room temperature and solvents are evaporated. The crude material is dissolved in dichloromethane and filtrated through a small silica cartridge, affording Compound (14) as mixture of oxime isomers, a yellow solid (55 mg; 55%). ¹H NMR (MeOH-d₄, 300 MHz) δ 2.25 (s, 3H), 2.50 (s, 3H), 6.65 (s, 1H), 7.12 (d, J=6 Hz, 1H), 7.40 (d, J=6 Hz, 1H), 7.72 (s, 1H). M⁻(ESI): 280.36; M⁺(ESI): 282.40. HPLC, Rt: 2.64 min (purity: 87.8%).

Example 15

N-[5-(5-cyano-2-thienyl)-4-methyl-1,3-thiazol-2-yl]acetamide (15)

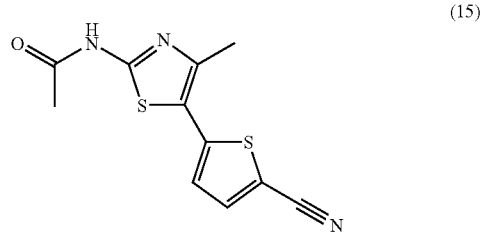

(15)

N-(5-{5-[(hydroxyimino)methyl]-2-thienyl}-4-methyl-1,3-thiazol-2-yl)acetamide, Compound (14) (100 mg; 0.36 mmol; 1 eq.), is heated with copper acetate (3.3 mg; 0.018 mmol; 0.05 eq.) in neat pyridine (5 ml) at 75° C. for 1 hour. Reaction mixture is cooled down to room temperature and solvents are evaporated to dryness. The crude material is dissolved in dichloromethane, washed with water (10 ml) and dried over MgSO$_4$. After evaporation of the solvents, the crude product is purified by flash chromatography using cyclohexane/ethyl acetate (90/10) as eluent. Compound (15) is obtained as a yellow powder (42 mg; 44%). $^1$H NMR (CDCl$_3$, 300 MHz) δ 2.22 (s, 3H), 2.43 (s, 3H), 7.01 (d, J=6 Hz, 1H), 7.50 (d, J=6 Hz, 1H). M-(ESI): 262.3; M$^+$(ESI): 264.3. HPLC, Rt: 3.03 min (purity: 91%).

Example 16 methyl 5-[2-(acetylamino)-4-methyl-1,3-thiazol-5-yl]thiophene-2-carboxylate (16)

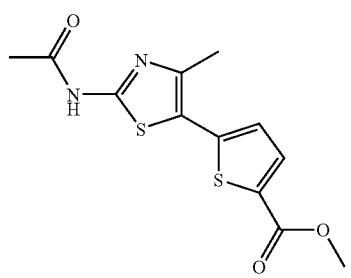

(16)

In a microwave tube, N-(5-iodo-4-methyl-1,3-thiazol-2-yl)acetamide, Intermediate 1 (150 mg; 0.53 mmol; 1 eq) and Pd(dppf)Cl$_2$ (19.5 mg; 0.03 mmol; 0.05 eq.) are suspended in Toluene (3 ml). Potassium fluoride (123.6 mg; 2.13 mmol; 4 eq.) is dissolved in MeOH (3 ml) and is added to the first solution. Methyl 5-(4,4,5,5-tetramethyl-1,3,2-dioxaborolan-2-yl)thiophene-2-carboxylate, Intermediate 2 (213.8 mg; 0.80 mmol; 1.50 eq.) is finally added. The resulting solution is flushed with argon, the tube is closed and heated under microwave action at 120° C. for 10 minutes. The desired product is formed together with [2,2']-bithiophenyl-5,5'-dicarboxylic acid dimethyl ester, the homocoupling product of methyl 5-(4,4,5,5-tetramethyl-1,3,2-dioxaborolan-2-yl)thiophene-2-carboxylate. Solvents are evaporated and the crude product is purified by preparative HPLC, affording Compound (16) as white-off solid (180 mg; 57%). $^1$H NMR (DMSO-d$^6$) δ 2.15 (s, 3H), 2.45 (s, 3H), 3.82 (s, 3H, OCH$_3$), 7.24 (d, J=4.5 Hz, 1H), 7.76 (d, J=4.5 Hz, 1H), 12.31 (s, 1H). M-(ESI): 295.10; M$^+$(ESI): 297.12. HPLC, Rt: 3.21 min (purity: 99.6%).

Example 17

N-[5-[5-(aminosulfonyl)-2-thienyl]-4-methyl-1,3-thiazol-2-yl]acetamide (17)

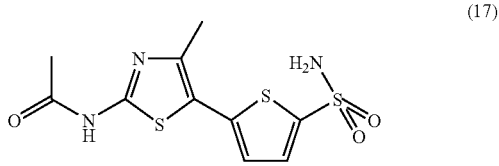

(17)

5-[2-(acetylamino)-4-methyl-1,3-thiazol-5-yl]thiophene-2-sulfonyl chloride, prepared as in Step 1 of Example 9 (200 mg; 0.59 mmol; 1 eq.), is dissolved in DCM (10 ml). A solution of ammonia in MeOH (0.59 ml; 2 M; 1.19 mmol; 2 eq.) and DIEA (460.4 mg; 3.56 mmol; 6 eq.) are added. After one hour, the solvents are evaporated. The crude product is purified by preparative HPLC, affording Compound (17) as white-off solid (36 mg; 17%). $^1$H NMR (DMSO-d$^6$) δ 2.14 (s, 3H), 2.42 (s, 3H), 7.16 (d, J=4.5 Hz, 1H), 7.50 (d, J=4.5 Hz, 1H), 7.72 (s, 2H), 12.30 (s, 1H). M-(ESI): 316.07; M$^+$(ESI): 318.10. HPLC, Rt: 2.16 min (purity: 99.8%).

Example 18

N-{5-[5-(1,4-dioxa-8-azaspiro[4,5]dec-8-ylsulfonyl)-2-thienyl]-4-methyl-1,3-thiazol-2-yl}acetamide (18)

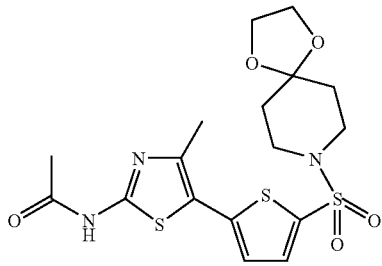

(18)

5-[2-(acetylamino)-4-methyl-1,3-thiazol-5-yl]thiophene-2-sulfonyl chloride, prepared as in Step 1 of example 9 (200 mg; 0.59 mmol; 1 eq.), is dissolved in DCM (10 ml). 1,4-Dioxa-8-azaspiro[4.5]decane (170.0 mg; 1.19 mmol; 2 eq.) and DIEA (460.4 mg; 3.56 mmol; 6 eq.) are added. After one hour, the solvents are evaporated. The crude product is purified by preparative HPLC, affording Compound (18) as yellow solid (96 mg; 37%). $^1$H NMR (DMSO-d$^6$) δ 1.66-1.78 (m, 4H), 2.15 (s, 3H), 2.45 (s, 3H), 3-3.15 (m, 4H), 3.83 (s, 4H), 7.31 (d, J=3.8 Hz, 1H), 7.61 (d, J=3.8 Hz, 1H), 12.15 (br s, 1H). M-(ESI): 444.25; M$^+$(ESI): 442.23. HPLC, Rt: 3.39 min (purity: 99.6%).

Example 19

N-[4-methyl-5-(3-thienyl)-1,3-thiazol-2-yl]acetamide (19)

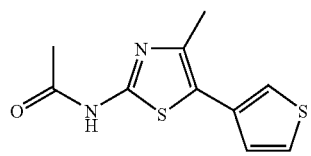

In a microwave tube, N-(5-iodo-4-methyl-1,3-thiazol-2-yl)acetamide, Intermediate 1 (564.2 mg; 2 mmol; 1 eq.) and Pd(dppf)Cl$_2$ (73.2 mg; 0.10 mmol; 0.05 eq.) are suspended in Toluene (7 ml). A solution of potassium fluoride (464.8 mg; 8 mmol; 4 eq.) in MeOH (7 ml) is added. 3-(4,4,5,5-Tetramethyl-1,3,2-dioxaborolan-2-yl)thiophene (630.3 mg; 3 mmol; 1.50 eq.) is finally added as a solid. The resulting solution is flushed with argon, the tube is closed and heated under microwave action at 120° C. for 15 minutes. The reaction mixture is filtered over Celite and the solvents are evaporated. The resulting crude product is dissolved in EtOAc, washed with water and brine and dried over MgSO$_4$. It is then purified by preparative HPLC, affording Compound (19) as white-off solid (316.7 mg; 66% yield). $^1$H NMR (DMSO-d$^6$) δ 2.12 (s, 3H), 2.35 (s, 3H), 7.28 (dd, J=1.5, 4.9 Hz, 1H), 7.58 (dd, J=1.5, 3.0 Hz, 1H), 7.67 (dd, J=3.0, 4.9 Hz, 1H), 12.09 (s, 1H). M$^-$(ESI): 237.03; M$^+$(ESI): 239.03. HPLC, Rt: 2.92 min (purity: 99.6%).

Example 20

Biological Assays

The compounds of the present invention may be subjected to the following assays:

a) High Throughput PI3K Lipid Kinase Assay (Binding Assay):

The efficacy of compounds of the invention in inhibiting the PI3K induced-lipid phosphorylation may be tested in the following binding assay The assay combines the scintillation proximity assay technology (SPA, Amersham) with the capacity of neomycin (a polycationic antibiotic) to bind phospholipids with high affinity and specificity. The Scintillation Proximity Assay is based on the properties of weakly emitting isotopes (such as $^3$H, $^{125}$I, $^{33}$P). Coating SPA beads with neomycin allows the detection of phosphorylated lipid substrates after incubation with recombinant PI3K and radioactive ATP in the same well, by capturing the radioactive phospholipids to the SPA beads through their specific binding to neomycin.

To a 384 wells MTP containing 5 μl of the test compound of Formula (I) (solubilized in 6% DMSO; to yield a concentration of 100, 30, 10, 3, 1, 0.3, 0.1, 0.03, 0.01, 01 μM of the test compound), the following assay components are added. 1) 5 μl (58 ng) of Human recombinant GST-PI3Kγ (in Hepes 40 mM, pH 7.4, DTT 1 mM and ethylenglycol 5%) 2) 10 μl of lipid micelles and 3) 10 μl of Kinase buffer ([$^{33}$P]γ-ATP 45 μM/60 nCi, MgCl$_2$ 30 mM, DTT 1 mM, β-Glycerophosphate 1 mM, Na$_3$VO$_4$ 100 μM, Na Cholate 0.3%, in Hepes 40 mM, pH 7.4). After incubation at room temperature for 180 minutes, with gentle agitation, the reaction is stopped by addition of 60 μl of a solution containing 100 μg of neomycin-coated PVT SPA beads in PBS containing ATP 10 mM and EDTA 5 mM. The assay is further incubated at room temperature for 60 minutes with gentle agitation to allow binding of phospholipids to neomycin-SPA beads. After precipitation of the neomycin-coated PVT SPA beads for 5 minutes at 1500×g, radioactive PtdIns(3)P is quantified by scintillation counting in a Wallac MicroBeta™ plate counter.

The values indicated in Table I below refer to the IC$_{50}$ (nM) with respect to PI3Kγ, i.e. the amount necessary to achieve 50% inhibition of said target. Said values show a considerable inhibitory potency of thiazole compounds with regard to PI3Kγ.

Examples of inhibitory activities for compounds of the invention are set out in Table I below.

TABLE I

IC$_{50}$ values of thiazole derivatives against PI3Kγ.

| Example No | PI3Kγ IC$_{50}$ (μM) |
|---|---|
| 1 | 0.215 |
| 3 | 0.219 |
| 5 | 0.249 |
| 8 | 1.098 | b) Cell Based ELISA to Monitor PI3K Inhibition:

The efficacy of compounds of the invention in inhibiting the PI3K induced Akt/PKB phosphorylation may be tested in the following cell based assay.

Measurement of Akt/PKB phosphorylation in macrophages after stimulation with Complement 5a: Raw 264: Raw 264-7 macrophages (cultured in DMEM-F12 medium containing 10% Fetal Calf serum and antibiotics) are plated at 20'000 cells/well in a 96 MTP 24 h before cell stimulation. Prior to the stimulation with 50 mM of Complement 5a during 5 minutes, Cells are serum starved for 2 h, and pretreated with inhibitors for 20 minutes. After stimulation cells are fixed in 4% formaldehyde for 20 minutes and washed 3 times in PBS containing 1% Triton X-100 (PBS/Triton). Endogenous peroxidase is blocked by a 20 minutes incubation in 0.6% H$_2$O$_2$ and 0.1% Sodium Azide in PBS/Triton and washed 3 times in PBS/Triton. Cells are then blocked by 60 minutes incubation with 10% fetal calf serum in PBS/Triton. Next, phosphorylated Akt/PKB is detected by an overnight incubation at 4° C. with primary antibody (anti phospho Serine 473 Akt IHC, Cell Signaling) diluted 800-fold in PBS/Triton, containing 5% bovine serum albumin (BSA). After 3 washes in PBS/Triton, cells are incubated for 60 minutes with a peroxidase conjugated goat-anti-rabbit secondary antibody (1/400 dilution in PBS/Triton, containing 5% BSA), washed 3 times in PBS/Triton, and 2 times in PBS and further incubated in 100 μl of luminescent substrate reagent solution (Pierce) for 2 minutes, followed by the reading (1 s/well).

The values indicated in Table II below reflect the percentage of inhibition of AKT phosphorylation as compared to basal level. Said values show a clear effect of the thiazole compounds on the activation of AKT phosphorylation in macrophages.

Examples of inhibitory activities for compounds of the invention are set out in Table II below.

TABLE II

IC$_{50}$ values of thiazole derivatives in Cell Assay

| Example No | Cell Assay (P-Akt, Elisa) IC$_{50}$ [nM] |
|---|---|
| 12 | 322 |

Example 21

Thioglycollate-induced Peritoneal Cavity Cell Recruitment Model

The in vivo efficacy of compounds of the invention in inhibiting the migration of leukocytes upon intraperitoneal challenge of thioglycollate may be tested with the following assay.

Experimental Protocol:

8-10 weeks old female C3H mice are fasted during 18 hours. 15 minutes prior the intraperitoneal injection of thioglycollate (1.5%, 40 ml/kg), the mice are treated orally with Thiazoles of Formula (I). Control mice receive CMC/Tween as vehicle (10 ml/kg). The mice are then sacrificed by $CO_2$ inhalation and the peritoneal cavity is washed two times with 5 ml of ice-cold PBS/1 mM EDTA. The ravages are done 4 hours or 48 hours after thioglycollate challenge to evaluate neutrophils or macrophages recruitment, respectively. The white blood cells (neutrophils, lymphocytes or macrophages) are counted using a Beckman Coulter® A°T 5diff™.

Dexamethasone is used as reference drug.

Examples of inhibitory activities for compounds are set out in Table III below.

TABLE III

| % of inhibition of Neutrophils recruitment at 10 mg/kg after 4 hours | |
| --- | --- |
| Example No | % of Inhibition |
| 12 | 38 |

Example 22

Preparation of a Pharmaceutical Formulation

Formulation 1—Tablets

A compound of Formula (I) is admixed as a dry powder with a dry gelatin binder in an approximate 1:2 weight ration. A minor amount of magnesium stearate is added as a lubricant.

The mixture is formed into 240-270 mg tablets (80-90 mg) of active thiazole compound per tablet) in a tablet press.

Formulation 2—Capsules

A compound of Formula (I) is admixed as a dry powder with a starch diluent in an approximate 1:1 weight ratio. The mixture is filled into 250 mg capsules (125 mg of active thiazole compound per capsule).

Formulation 3—Liquid

A compound of Formula (I) (1250 mg), sucrose (1.75 g) and xanthan gum (4 mg) are blended, passed through a No. 10 mesh U.S. sieve, and then mixed with a previously prepared solution of microcrystalline cellulose and sodium carboxymethyl cellulose (11:89, 50 mg) in water. Sodium benzoate (10 mg), flavor, and color are diluted with water and added with stirring. Sufficient water is then added to produce a total volume of 5 ml.

Formulation 4—Tablets

A compound of Formula (I) is admixed as a dry powder with a dry gelatin binder in an approximate 1:2 weight ratio. A minor amount of magnesium stearate is added as a lubricant. The mixture is formed into 450-900 mg tablets (150-300 mg of active thiazole compound) in a tablet press.

Formulation 5—Injection

A compound of Formula (I) is dissolved in a buffered sterile saline injectable aqueous medium to a concentration of approximately 5 mg/ml.

The invention claimed is

1. A thiazole derivative according to Formula (I),

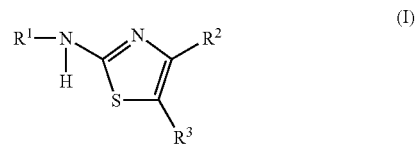

(I)

wherein $R^1$ is selected from cycloalkyl or acyl;
$R^2$ is selected from H, halogen, $C_1$-$C_6$-alkyl, $C_2$-$C_6$-alkenyl or $C_2$-$C_6$-alkynyl;
$R^3$ is selected from the following thienyl groups:

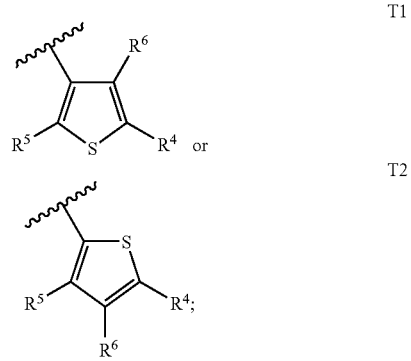

$R^4$ is selected from $C_2$-$C_6$-alkenyl, $C_2$-$C_6$-alkynyl, alkoxycarbonyl, sulfonyl or acyl;
$R^5$ and $R^6$ are independently selected from H, $C_1$-$C_6$-alkyl, $C_2$-$C_6$-alkenyl, $C_2$-$C_6$-alkynyl or halogen;
and isomers, enantiomers, diastereomers, racemates and pharmaceutically acceptable salts thereof.

2. The thiazole derivative according to claim 1, wherein $R^1$ is acyl.

3. The thiazole derivative according to claim 1, wherein $R^2$ is methyl.

4. The thiazole derivative according to claim 1, wherein $R^3$ is a thienyl T1.

5. The thiazole derivative according to claim 1, wherein $R^3$ is a thienyl T2.

6. The thiazole derivative according to claim 1, wherein $R^4$ is selected from $C_2$-$C_6$-alkenyl or $C_2$-$C_6$-alkynyl.

7. The thiazole derivative according to claim 1, wherein $R^4$ is sulfonyl.

8. The thiazole derivative according to claim 1, wherein $R^4$ is selected from alkoxycarbonyl or acyl.

9. The thiazole derivative according to claim 1, wherein $R^5$ and $R^6$ are H.

10. The thiazole derivative according to claim 1, said thiazole derivative being selected from:
N-[5-(5-formyl-2-thienyl)-4-methyl-1,3-thiazol-2-yl]acetamide;
N-(5-{5-[(allylamino)methyl]-2-thienyl}-4-methyl-1,3-thiazol-2-yl)acetamide;

N-{5-[5-(hydroxymethyl)-2-thienyl]-4-methyl-1,3-thiazol-2-yl}acetamide;

5-[2-(acetylamino)-4-methyl-1,3-thiazol-5-yl]thiophene-2-carboxylic acid;

N-{4-methyl-5-[5-(morpholin-4-ylcarbonyl)-2-thienyl]-1,3-thiazol-2-yl}acetamide;

N-[4-methyl-5-(2-thienyl)-1,3-thiazol-2-yl]acetamide;

N-(5-{5-[(4-hydroxypiperidin-1-yl)carbonyl]-2-thienyl}-4-methyl-1,3-thiazol-2-yl) acetamide;

N-(5-{5-[(3-hydroxypiperidin-1-yl)carbonyl]-2-thienyl}-4-methyl-1,3-thiazol-2-yl) acetamide;

N-(5-{5-[(3-hydroxypiperidin-1-yl)sulfonyl]-2-thienyl}-4-methyl-1,3-thiazol-2-yl) acetamide;

N-(5-{5-[(4-hydroxypiperidin-1-yl)sulfonyl]-2-thienyl}-4-methyl-1,3-thiazol-2-yl) acetamide;

N-[5-(5-{[(2-hydroxyethyl)amino]sulfonyl}-2-thienyl)-4-methyl-1,3-thiazol-2-yl]acetamide;

N-(5-{5-[(allylamino)sulfonyl]-2-thienyl}-4-methyl-1,3-thiazol-2-yl)acetamide;

N-{4-methyl-5-[5-(morpholin-4-ylsulfonyl)-2-thienyl]-1,3-thiazol-2-yl}acetamide;

N-(5-{5-[(E)-(hydroxyimino)methyl]-2-thienyl}-4-methyl-1,3-thiazol -2-yl)acetamide;

N-[5-(5-cyano-2-thienyl)-4-methyl-1,3-thiazol-2-yl]acetamide;

Methyl 5-[2-(acetylamino)-4-methyl-1,3-thiazol-5-yl]thiophene-2-carboxylate;

N-{5-[5-(aminosulfonyl)-2-thienyl]-4-methyl-1,3-thiazol-2-yl}acetamide; or

N-{5-[5-(1,4-dioxa-8-azaspiro[4.5]dec-8-ylsulfonyl)-2-thienyl]-4-methyl-1,3-thiazol-2-yl}acetamide.

11. A pharmaceutical composition comprising a compound according to claim 1 and a pharmaceutically acceptable carrier, diluent or excipient thereof.

* * * * *

UNITED STATES PATENT AND TRADEMARK OFFICE
CERTIFICATE OF CORRECTION

PATENT NO.        : 7,888,379 B2                                Page 1 of 3
APPLICATION NO.   : 11/915508
DATED             : February 15, 2011
INVENTOR(S)       : Anna Quattropani et al.

It is certified that error appears in the above-identified patent and that said Letters Patent is hereby corrected as shown below:

Column 2,
Line 42, "(PI(4,5)P2)" should read --(PI(4,5)P$_2$)--.
Lines 45-46, "(PI(3,4)P2) and phosphatidylinositol 3,4,5-trisphosphate (PI(3,4,5)P3" should read --(PI(3,4)P$_2$) and phosphatidylinositol 3,4,5-trisphosphate (PI(3,4,5)P$_3$--.

Column 3,
Line 48, "chamomiles" should read --chemokines--.

Column 4,
Line 25, "it can longer" should read --it can no longer--.
Line 39, "G(I)-coupled" should read --G(i)-coupled--.
Line 42, "chamomiles" should read --chemokines--.

Column 6,

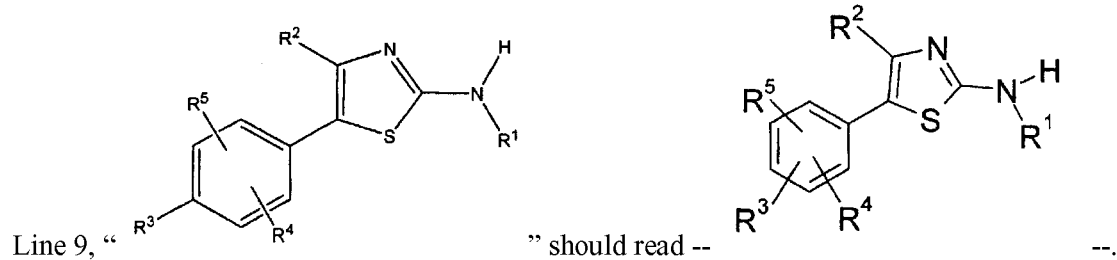

Line 9, " " should read -- --.

Column 7,
Line 29, "αand" should read --α and--.
Line 32, "at least one a compound" should read --at least one compound--.

Column 10,
Line 15, "2-(N-methylureido)ethyl" should read --2-(N'-methylureido)ethyl--.
Lines 34-35, "group –N$^+$R'R", where" should read --group –N$^+$RR'R", where--.

Signed and Sealed this
Seventh Day of June, 2011

David J. Kappos
*Director of the United States Patent and Trademark Office*

Column 11,
Line 64, "the like" should read --the like.--.

Column 13,
Lines 42-47, "carbonyl);
>>In still another embodiment according to the invention, the compounds of Formula (I) are useful for the treatment and/or prophylaxis of chronic obstructive pulmonary disease, anaphylactic
$R^5$ and $R^6$"
should read --carbonyl);
>>$R^5$ and $R^6$--.

Column 15,
Line 10, "cell anaemia. shock," should read
--cell anaemia.
>>In still another embodiment according to the invention, the compounds of Formula (I) are useful for the treatment and/or prophylaxis of chronic obstructive pulmonary disease, anaphylactic shock,--.

Column 17,
Line 38, "pathways for the will be described" should read --pathways will be described--.

Column 25,
Line 5, "NaHB(OAc) or" should read --NaHB(OAc)$_3$ or--.
Line 17, "wherein $R^4$CHNOH)" should read --wherein $R^4$ = CHNOH)--.

Column 34,
Lines 39-40, "N-[5-[5-(hydroxymethyl)-2-thienyl]-4-methyl-1,3-thiazol-2-yl]acetamide (3)" should read --N-{5-[5-(hydroxymethyl)-2-thienyl]-4-methyl-1,3-thiazol-2-yl}acetamide (3)--.

Column 35,

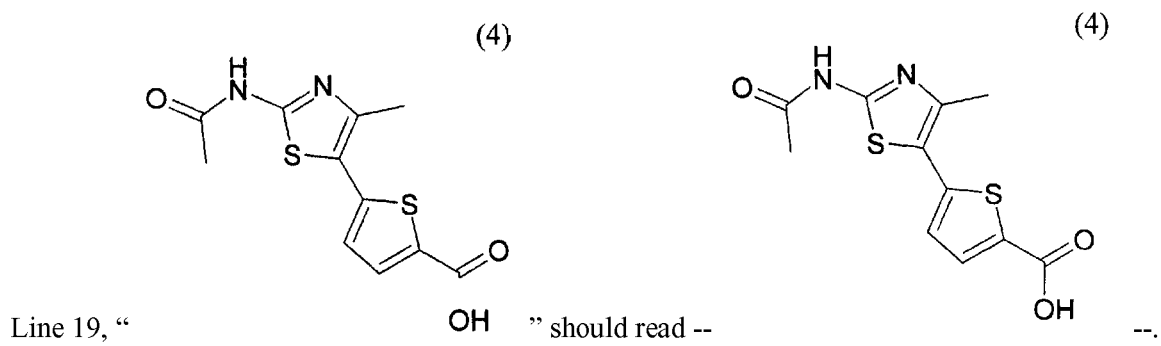

Line 19, "                    " should read --                    --.

Column 37,
Line 41, "3.864" should read --3.86-4--.

Column 38,
Lines 17-18, "Step 2: N-(5-[(5-[(3-hydroxypiperdin-1-yl)sulfonyl]-2-thienyl]-4-methyl-1,3-thiazol-2-yl)acetamide (9)" should read --Step 2: N-(5-{5-[(3-hydroxypiperdin-1-yl)sulfonyl]-2-thienyl}-4-methyl-1,3-thiazol-2-yl)acetamide (9)--.
Lines 40-41, "N-(5-[5-[(4-hydroxypiperdin-1-yl)sulfonyl]-2-thienyl]-4-methyl-1,3-thiazol-2-yl)acetamide (10)" should read --N-(5-{5-[(4-hydroxypiperdin-1-yl)sulfonyl]-2-thienyl}-4-methyl-1,3-thiazol-2-yl)acetamide (10)--.

Column 39,
Lines 41-42, "N-(5-[5-{(allylamino)sulfonyl]-2-thienyl}-4-methyl-1,3-thiazol-2-yl)acetamide (12)" should read --N-(5-{5-[(allylamino)sulfonyl]-2-thienyl}-4-methyl-1,3-thiazol-2-yl)acetamide (12)--.

Column 42,
Lines 10-11, "N-[5-[5-(aminosulfonyl)-2-thienyl]-4-methyl-1,3-thiazol-2-yl]acetamide (17)" should read --N-{5-[5-(aminosulfonyl)-2-thienyl]-4-methyl-1,3-thiazol-2-yl}acetamide (17)--.

Column 43,
Line 44, "assay" should read --assay.--.

Column 45,
Line 18, "The ravages" should read --The lavages--.